United States Patent
Sato et al.

(10) Patent No.: US 10,085,650 B2
(45) Date of Patent: Oct. 2, 2018

(54) MEASUREMENT DEVICE, MEASUREMENT METHOD, AND RECORDING MEDIUM STORING A MEASUREMENT PROGRAM

(71) Applicant: OMRON HEALTHCARE CO., LTD., Muko-shi, Kyoto (JP)

(72) Inventors: Hironori Sato, Kyoto (JP); Hideo Utsuno, Kyoto (JP); Hiroshi Matsuhisa, Kyoto (JP); Keisuke Yamada, Kyoto (JP); Toshihiko Ogura, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 317 days.

(21) Appl. No.: 14/353,475

(22) PCT Filed: Oct. 22, 2012

(86) PCT No.: PCT/JP2012/077213
§ 371 (c)(1),
(2) Date: Apr. 22, 2014

(87) PCT Pub. No.: WO2013/061911
PCT Pub. Date: May 2, 2013

(65) Prior Publication Data
US 2014/0257117 A1    Sep. 11, 2014

(30) Foreign Application Priority Data

Oct. 28, 2011 (JP) .................................. 2011-237583

(51) Int. Cl.
*A61B 5/02* (2006.01)
*A61B 5/021* (2006.01)
(Continued)

(52) U.S. Cl.
CPC .......... *A61B 5/02014* (2013.01); *A61B 5/022* (2013.01); *A61B 5/024* (2013.01);
(Continued)

(58) Field of Classification Search
CPC ........................ A61B 5/02125; A61B 5/02014
(Continued)

(56) References Cited

U.S. PATENT DOCUMENTS 4,008,711 A    2/1977  Olinger et al.
6,331,162 B1 * 12/2001 Mitchell ....................... 600/485
(Continued)

FOREIGN PATENT DOCUMENTS

JP    A-05-023335    2/1993
JP    A-2004-049331  2/2004
(Continued)

OTHER PUBLICATIONS

Sato et al., "An Estimation Method of Arterial Pathology by Pulse Wave Propagation Measurements", Nov. 2010, pp. 425-428.*
(Continued)

*Primary Examiner* — Puya Agahi
(74) *Attorney, Agent, or Firm* — Oliff PLC

(57) ABSTRACT

A measurement device includes a detection device to detect a pulse wave signal at a first measurement location in a vascular pathway from the heart of a measurement subject to an area where an arterial aneurysm is predicted to occur and a pulse wave signal at a second measurement location in a vascular pathway from the heart of the measurement subject to an area that is different from the area where an arterial aneurysm is predicted to occur, a comparison device to calculate a comparison result by comparing frequency characteristics between the pulse wave signals, and a determination device to determine at least one of the presence/absence and size of an arterial aneurysm based on a
(Continued)

(CROSS SECTIONAL VIEW)

(SIDE VIEW)

predetermined characteristic amount for a frequency contained in the comparison result.

12 Claims, 24 Drawing Sheets

(51) Int. Cl.
    *A61B 5/022* (2006.01)
    *A61B 5/024* (2006.01)
    *A61B 5/00* (2006.01)
(52) U.S. Cl.
    CPC ........ *A61B 5/02125* (2013.01); *A61B 5/7246* (2013.01); *A61B 5/7282* (2013.01); *A61B 5/6828* (2013.01); *A61B 5/7257* (2013.01)
(58) Field of Classification Search
    USPC ................. 600/301, 481, 485, 490–504
    See application file for complete search history.

(56) References Cited

U.S. PATENT DOCUMENTS

| | | | |
|---|---|---|---|
| 2004/0171940 A1 | 9/2004 | Narimatsu | |
| 2008/0262362 A1* | 10/2008 | Kolluri et al. | 600/490 |
| 2009/0204013 A1* | 8/2009 | Muhlsteff | A41B 9/001 600/506 |
| 2010/0113960 A1* | 5/2010 | Scheib | A61B 5/4821 600/544 |
| 2010/0121204 A1 | 5/2010 | Utsuno et al. | |
| 2013/0109982 A1* | 5/2013 | Sato | A61B 5/02014 600/502 |

FOREIGN PATENT DOCUMENTS

| | | | |
|---|---|---|---|
| JP | A-2004-261319 | 9/2004 | |
| JP | A-2007-222626 | 9/2007 | |
| JP | A-2008-246010 | 10/2008 | |
| JP | A-2009-112428 | 5/2009 | |
| JP | A-2010-284517 | 12/2010 | |
| JP | WO 2012011463 A1 * | 1/2012 | ......... A61B 5/02014 |

OTHER PUBLICATIONS

Sato et al., "An Estimation Method of Arterial Pathology by Pulse Wave Propagation Measurements," *Symposium on Sports Engineering: Symposium on Human Dynamics*, Nov. 2, 2010, pp. 425-428 (w/ abstract).

International Search Report issued in International Application No. PCT/JP2012/077213 dated Nov. 20, 2012.

International Preliminary Report on Patentability issued in International Patent Application No. PCT/JP2012/077213 dated Jun. 18, 2013 (w/ translation).

* cited by examiner (CROSS SECTIONAL VIEW)

(SIDE VIEW)

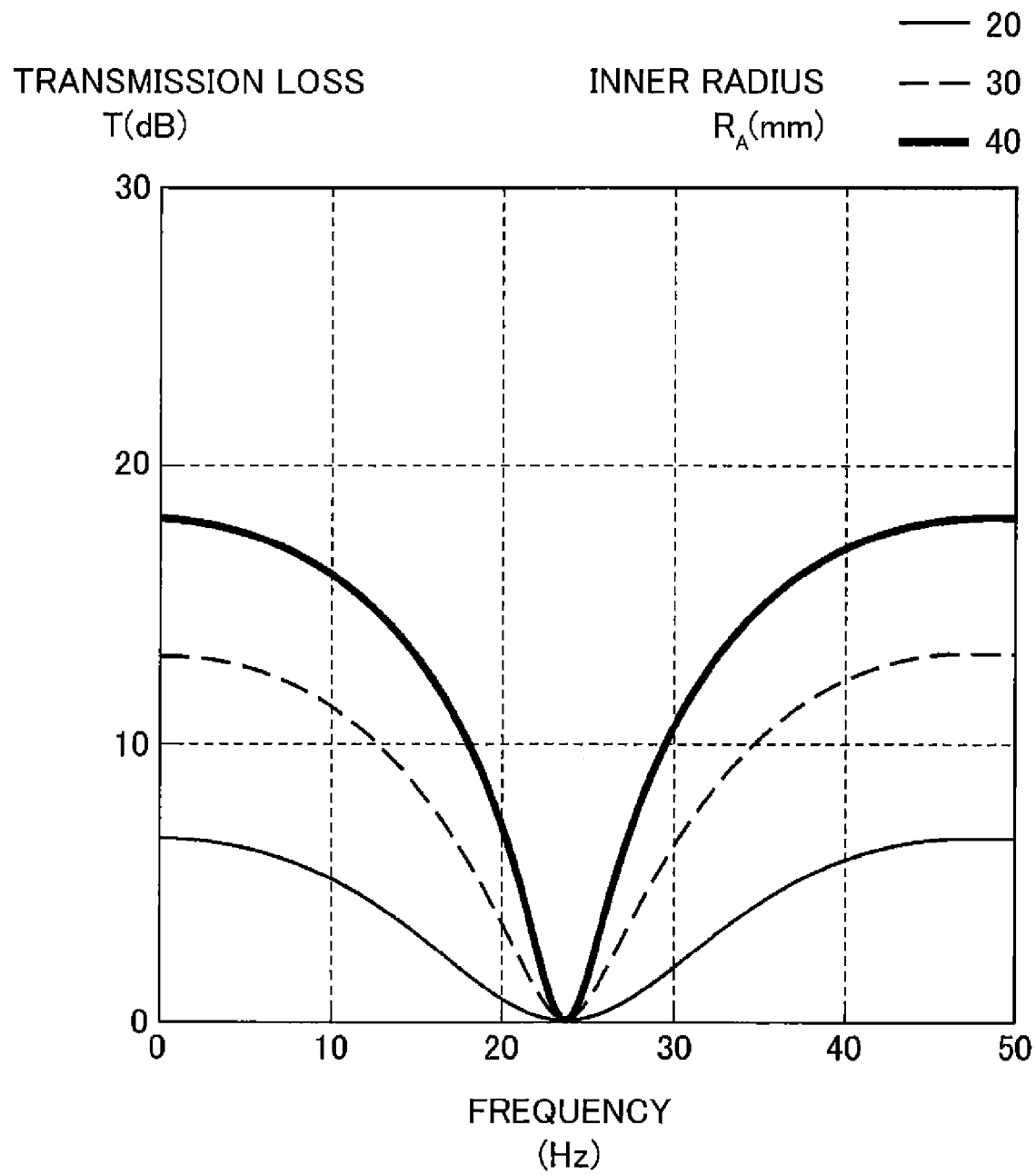

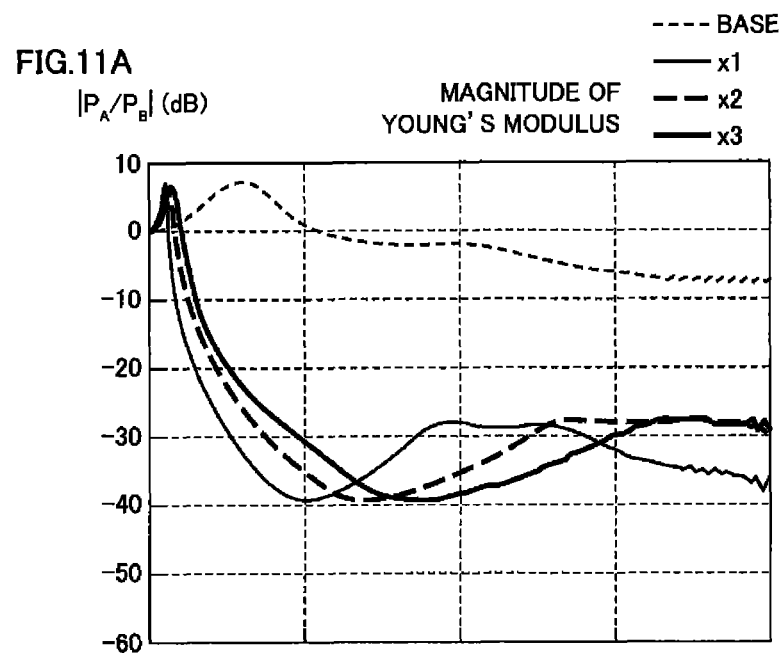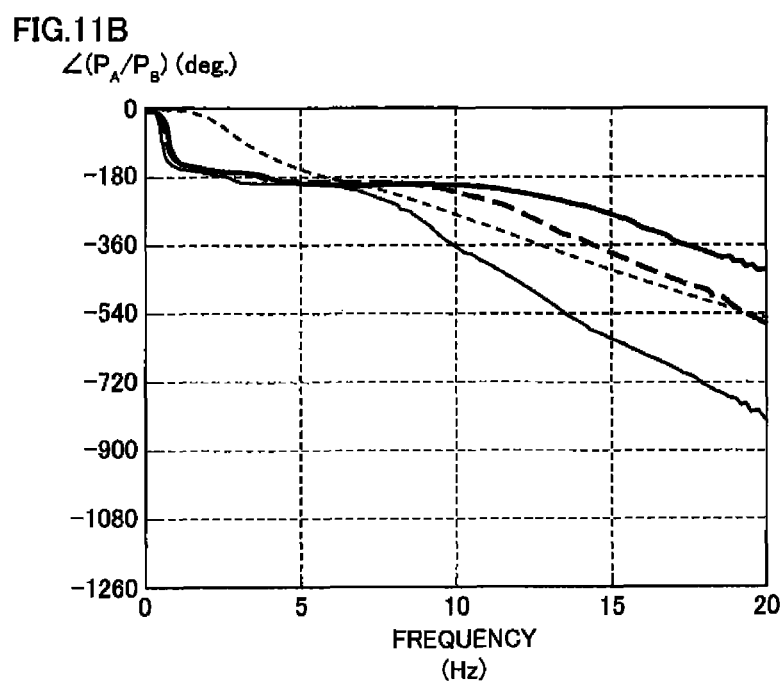

MEASUREMENT DEVICE, MEASUREMENT METHOD, AND RECORDING MEDIUM STORING A MEASUREMENT PROGRAM

TECHNICAL FIELD

The present invention relates to measurement devices, measurement methods, and recording media that store measurement programs for evaluating arterial aneurysms that can occur in vascular pathways.

BACKGROUND ART

Arterial aneurysm can be given as an example of a pathologic change occurring in a vascular pathway. Aortic aneurysm, which is an arterial aneurysm occurring particularly in the abdominal area, has no early symptoms, and unless unintentionally discovered during an MRI (magnetic resonance imaging), CT (computed tomography), ultrasound, or similar scan, is often discovered just before rupture, during an abdominal surge or the like. It is therefore desirable to detect such a condition early through a casual examination, such as during a health checkup.

JP H05-023335A (Patent Literature 1) discloses a device that makes diagnoses using ultrasound waves, as a device for detecting aortic aneurysms. Meanwhile, JP 2007-222626A (Patent Literature 2) discloses a method of detecting a pathologic change as a specific site by comparing multiple pieces of image data taken through X-ray CT, MRI, or similar scans.

CITATION LIST

Patent Literature

Patent Literature 1: JP H05-023335A
Patent Literature 2: JP 2007-222626A

SUMMARY OF INVENTION

Technical Problem

However, with the ultrasound wave diagnostic device disclosed in Patent Literature 1, it is necessary to take sequential measurements of the aorta based on the likelihood that an arterial aneurysm is present. On the other hand, the method disclosed in Patent Literature 2 requires that an image of the blood vessels throughout the entire body has been captured in advance through X-ray CT, MRI, or similar scans. The devices for detecting arterial aneurysms, the details of the examinations, and so on are complex with either of these conventional techniques. Thus it is unrealistic in terms of time, cost, and the like to include arterial aneurysm examinations as items to be examined in periodic health checkups and the like, which makes it difficult to discover aortic aneurysms before they progress to serious conditions.

Having been achieved in light of the aforementioned problems, it is an object of the present invention to provide a measurement device, a measurement method, and a recording medium storing a measurement program that are capable of evaluating the presence and/or size of an arterial aneurysm occurring in a vascular pathway using a comparatively simple configuration and procedure.

Solution to Problem

A measurement device according to one aspect of the present invention includes a detection means for detecting a pulse wave signal at a first measurement location in a vascular pathway from the heart of a measurement subject to an area where an arterial aneurysm is predicted to occur and a pulse wave signal at a second measurement location in a vascular pathway from the heart of the measurement subject to an area that is different from the area where an arterial aneurysm is predicted to occur, a comparison means for calculating a comparison result by comparing frequency characteristics between the pulse wave signals, and a determination means for determining at least one of the presence/absence and size of an arterial aneurysm based on a predetermined characteristic amount for a frequency contained in the comparison result.

Preferably, the comparison means includes a means for calculating a transfer function between the first measurement location and the second measurement location.

Further preferably, the determination means determines the presence/absence of an arterial aneurysm based on a degree of variation in a phase in the phase difference characteristics of the transfer function.

Alternatively, the comparison means preferably includes a means for calculating a phase delay time for each frequency in the pulse wave signals, and the determination means determines at least one of the presence/absence and size of an arterial aneurysm based on a number of times the phase difference characteristics of the transfer function intersect with a phase angle calculated based on an average of the phase delay times calculated for each frequency.

Further preferably, the determination means determines the size of an arterial aneurysm based on a frequency interval at which the phase difference characteristics of the transfer function intersect with the phase angle calculated based on an average of the phase delay times calculated for each frequency.

Alternatively, the comparison means preferably includes a means for calculating a phase delay time for each frequency in the pulse wave signals, and the determination means determines at least one of the presence/absence and size of an arterial aneurysm based on a frequency interval at which the phase difference characteristics of the transfer function intersect with a phase angle calculated based on an average of the phase delay times calculated for each frequency.

Alternatively, the determination means preferably determines at least one of the presence/absence and size of an arterial aneurysm based on a frequency interval at which an extreme value appears in gain characteristics of the transfer function.

Preferably, the comparison means includes a means for calculating frequency characteristics with respect to pulse wave propagation velocities between the pulse wave signals.

Further preferably, the determination means determines the presence/absence of an arterial aneurysm based on a degree of variation in the pulse wave propagation velocities found in the frequency characteristics with respect to the pulse wave propagation velocities.

Alternatively, the determination means preferably determines at least one of the presence/absence and size of an arterial aneurysm based on a frequency interval of a fluctuation in the pulse wave propagation velocities found in the frequency characteristics with respect to the pulse wave propagation velocities.

A measurement method according to another aspect of the present invention includes a step of detecting a pulse wave signal at a first measurement location in a vascular pathway from the heart of a measurement subject to an area where an arterial aneurysm is predicted to occur and a pulse wave signal at a second measurement location in a vascular pathway from the heart of the measurement subject to an area that is different from the area where an arterial aneurysm is predicted to occur, a step of calculating a comparison result by comparing frequency characteristics between the pulse wave signals, and a step of determining at least one of the presence/absence and size of an arterial aneurysm based on a predetermined characteristic amount for a frequency contained in the comparison result.

A recording medium in which is stored a measurement program according to another aspect of the present invention causes, when executed by a computer, the computer to execute a step of detecting a pulse wave signal at a first measurement location in a vascular pathway from the heart of a measurement subject to an area where an arterial aneurysm is predicted to occur and a pulse wave signal at a second measurement location in a vascular pathway from the heart of the measurement subject to an area that is different from the area where an arterial aneurysm is predicted to occur, a step of calculating a comparison result by comparing frequency characteristics between the pulse wave signals, and a step of determining at least one of the presence/absence and size of an arterial aneurysm based on a predetermined characteristic amount for a frequency contained in the comparison result.

Advantageous Effects of Invention

According to the present invention, the presence and/or size of an arterial aneurysm occurring in the vascular pathway can be evaluated using a comparatively simple configuration and procedure.

BRIEF DESCRIPTION OF DRAWINGS

FIG. 2 is a diagram illustrating a result of evaluating the effect of an inner radius of a middle section, calculated according to a transmission loss calculation formula according to the embodiment.

FIG. 11 is a gain diagram and phase diagram for a transfer function $P_A/P_B$ when the inner radius of the arterial aneurysm is fixed at 50 mm and an overall Young's modulus is varied.

DESCRIPTION OF EMBODIMENTS

Figure 1A:
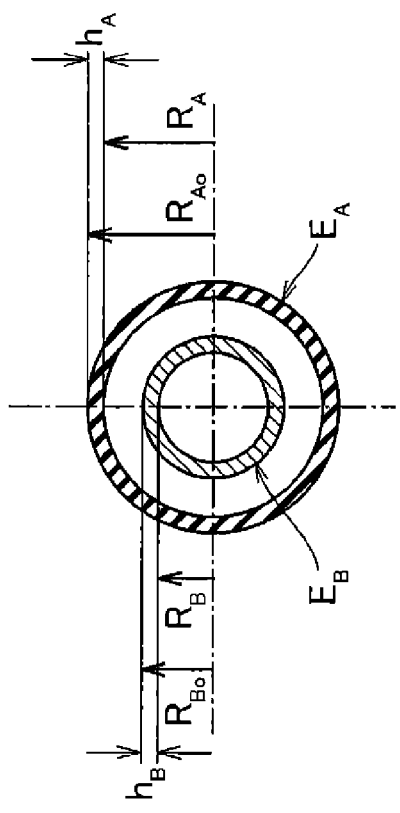
FIG. 1 is a diagram illustrating an arterial aneurysm model employed in an embodiment of the present invention.

Embodiments of the present invention will be described in detail hereinafter with reference to the drawings. Note that identical or corresponding elements in the drawings will be given the same reference numerals, and descriptions thereof will not be repeated.

A. Overview

A measurement method according to the present embodiment handles arterial aneurysm as a partial distension in a viscoelastic tube, and focuses on loss in pulse waves that travel therethrough. The presence/absence and/or size (inner radius and length) of an arterial aneurysm is evaluated based on changes in frequency characteristics by applying this arterial aneurysm model in a pulse wave propagation model for the human arterial system.

Such frequency characteristics are calculated based on, for example, pulse wave signals calculated in lower extremities (measurement locations in vascular pathways from a measurement subject's heart to areas where an arterial aneurysm is predicted to occur) and in upper extremities (measurement locations in vascular pathways from a measurement subject's heart to areas aside from the areas where an arterial aneurysm is predicted to occur).

B. Analysis Based on Pulse Wave Propagation Model b1: Modeling

In the present embodiment, the measurement subject's vascular pathway is divided into a plurality of segments, and a transfer function expressing the vascular pathway is calculated by modeling each segment using a one-dimensional linear distributed parameter model. The transfer function is calculated analytically from a mechanical model in which pulse waves propagate through blood vessels.

An arterial aneurysm is a pathologic change in which the inner diameter of a vascular pathway (artery) expands partway therethrough. A characteristic impedance of the vascular pathway changes in the range of the vascular pathway where the inner diameter has expanded. This is the same phenomenon as occurs in reactance silencers for sound waves, and results in the propagated pulse wave being dampened. In the present embodiment, this phenomenon is used to detect an arterial aneurysm. However, the vascular pathway differs from a reactance silencer in that the vascular pathway is a viscoelastic tube, and thus changes in the inner diameter cause the pulse wave propagation velocity to change in addition to the characteristic impedance. The present embodiment takes such changes in the pulse wave propagation velocity into consideration and focuses primarily on loss (transmission loss) when the propagated pulse wave travels through a range in which an arterial aneurysm is present.

Figure 1B:
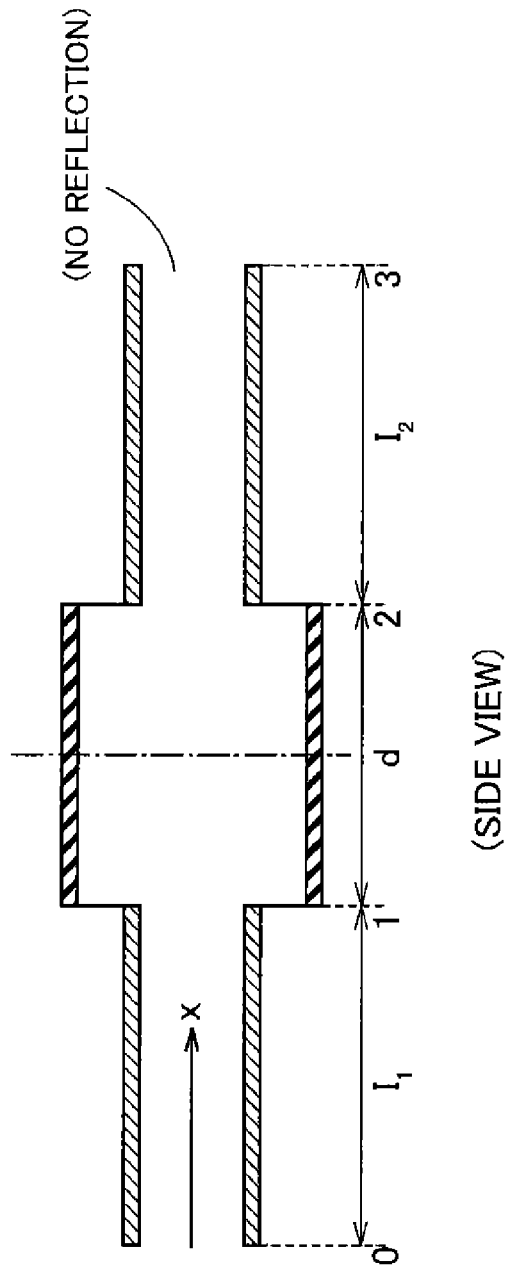

FIG. 1 is a diagram illustrating an arterial aneurysm model employed in an embodiment of the present invention. FIG. 1(A) is a cross-sectional view and FIG. 1(B) is a side view.

Referring to FIG. 1, the present embodiment assumes a vascular pathway having three segments, where an arterial aneurysm is present in a middle section thereof. In other words, it is assumed that the arterial aneurysm has occurred in a segment (1-2), and that segments (0-1) and (2-3) on either side thereof (both segments will be referred to as "peripheral sections" hereinafter) are healthy vascular pathways. The segment (1-2) is a model of a viscoelastic tube whose inner diameter has expanded.

In FIG. 1, for the segment (1-2) that serves as the middle section, a length is represented by d, a Young's modulus is represented by $E_A$, an inner radius is represented by $R_A$, an outer radius is represented by $R_{Ao}$, and a wall thickness is represented by $h_A$. Likewise, for the segments (0-1) and (2-3) that serve as the peripheral sections, the respective lengths are represented by $l_1$ and $l_2$, the Young's modulus is represented by $E_B$, the inner radius is represented by $R_B$, the outer radius is represented by $R_{Bo}$, and the wall thickness is represented by $h_B$. Points 0 and 3 are assumed to be ends with no reflection. Note that the following analysis indicates positions in the respective segments as distances x from the point 0 (with the right direction in the drawings being positive).

b2: Mathematical Analysis

Next, using the model shown in FIG. 1, a mathematical analysis will be described from the mechanical and physical standpoints regarding the propagation of pulse waves emitted from the heart.

A pressure $p_{01}(x,t)$ in the segment (0-1) can be expressed by the following Formula (1) using a progressive wave pressure $p_{f1}$ and a regressive wave pressure $p_{r1}$ at the point 0, a distance x from the point 0, and a propagation constant $\gamma_B$ of the peripheral sections.

$$p_{01}(x,t) = p_{f1}e^{-\gamma_B x} + p_{r1}e^{\gamma_B x} \tag{1}$$

Meanwhile, a volumetric flow rate $q_{01}(x,t)$ can be expressed by the following Formula (2) using a characteristic impedance $Z_{0B}$ of the peripheral sections.

$$q_{01}(x, t) = \frac{1}{Z_{0B}}(p_{f1}e^{-\gamma_B x} - p_{r1}e^{\gamma_B x}) \tag{2}$$

Likewise, a pressure $p_{12}(x,t)$ and a volumetric flow rate $q_{12}(x,t)$ of the segment (1-2) can be expressed by the following Formulas (3) and (4), respectively, using a progressive wave pressure $p_{f2}$ and a regressive wave pressure $p_{r2}$, a characteristic impedance $Z_{0A}$ of the middle section, a distance x from the point 0, and a propagation constant $\gamma_A$ of the middle section.

$$p_{12}(x, t) = p_{f2}e^{-\gamma_A x} + p_{r2}e^{\gamma_A x} \tag{3}$$

$$q_{12}(x, t) = \frac{1}{Z_{0A}}(p_{f2}e^{-\gamma_A x} - p_{r2}e^{\gamma_A x}) \tag{4}$$

Furthermore, a pressure $p_{23}(x,t)$ and a volumetric flow rate $q_{23}(x,t)$ of the segment (2-3) can be expressed by the following Formulas (5) and (6), using a progressive wave pressure $p_{f3}$, a distance x from the point 0, and the propagation constant $\gamma_B$ of the peripheral sections. Under conditions where the point 3 is an end with no reflection, a regressive wave pressure is not present, and thus it is only necessary to take the progressive wave pressure $p_{f3}$ into consideration.

$$p_{23}(x, t) = p_{f3}e^{-\gamma_B x} \tag{5}$$

$$q_{23}(x, t) = \frac{1}{Z_{0B}}p_{f3}e^{-\gamma_B x} \tag{6}$$

Next, the following formulas can be derived from conditions of continuity of the pressures and volumetric flow rates at the areas of connection between the respective segments.

That is, at the area of connection at point 1, the pressure on the side of the segment (0-1) is the same as the pressure on the side of the segment (1-2), and thus the following Formula (7) holds true, based on the aforementioned Formulas (1) and (3).

$$p_{f1}e^{-\gamma_B l_1} + p_{r1}e^{\gamma_B l_1} = p_{f2}e^{-\gamma_A l_1} + p_{r2}e^{\gamma_A l_1} \tag{7}$$

Likewise, at the area of connection at point 1, the volumetric flow rate on the side of the segment (0-1) is the same as the volumetric flow rate on the side of the segment (1-2), and thus the following Formula (8) holds true, based on the aforementioned Formulas (2) and (4).

$$\frac{1}{Z_{0B}}(p_{f1}e^{-\gamma_B l_1} - p_{r1}e^{\gamma_B l_1}) = \frac{1}{Z_{0A}}(p_{f2}e^{-\gamma_A l_1} - p_{r2}e^{\gamma_A l_1}) \tag{8}$$

In the same manner, at the area of connection at point 2, the pressure on the side of the segment (1-2) is the same as the pressure on the side of the segment (2-3), and thus the following Formula (9) holds true, based on the aforementioned Formulas (3) and (5).

$$p_{f2}e^{-\gamma_A(l_1+d)} + p_{r2}e^{\gamma_A(l_1+d)} = p_{f3}e^{-\gamma_B(l_1+d)} \tag{9}$$

Likewise, at the area of connection at point 2, the volumetric flow rate on the side of the segment (1-2) is the same as the volumetric flow rate on the side of the segment (2-3), and thus the following Formula (10) holds true, based on the aforementioned Formulas (4) and (6).

$$\frac{1}{Z_{0A}}\{p_{f2}e^{-\gamma_A(l_1+d)} - p_{r2}e^{\gamma_A(l_1+d)}\} = \frac{1}{Z_{0B}}p_{f3}e^{-\gamma_B(l_1+d)} \quad (10)$$

Here, Formula (10) is simplified for the characteristic impedance, and the sum with Formula (9) is found. Expressing the progressive wave pressure $p_{f2}$ in the segment (1-2) using the progressive wave pressure $p_{f3}$ in the segment 2-3 results in the following Formula (11).

$$p_{f2} = \frac{Z_{0A} + Z_{0B}}{2Z_{0B}} p_{f3} e^{(\gamma_A - \gamma_B)(l_1+d)} \quad (11)$$

The following Formula (12) is obtained by solving Formula (9) for the regressive wave pressure $p_{r2}$ in the segment (1-2) and substituting the result in Formula (11).

$$p_{r2} = \frac{Z_{0A} - Z_{0B}}{2Z_{0B}} p_{f3} e^{-(\gamma_A + \gamma_B)(l_1+d)} \quad (12)$$

Next, when Formulas (7) and (8) are simplified for the progressive wave pressure $p_{f1}$ in the segment (0-1), the following Formulas (13) and (14) are obtained.

$$p_{f1} + p_{r1} e^{2\gamma_B l_1} = p_{f2} e^{(\gamma_B - \gamma_A) l_1} + p_{r2} e^{(\gamma_A + \gamma_B) l_1} \quad (13)$$

$$p_{f1} - p_{r1} e^{2\gamma_B l_1} = \frac{Z_{0B}}{Z_{0A}} \{p_{f2} e^{(\gamma_B - \gamma_A) l_1} + p_{r2} e^{(\gamma_A + \gamma_B) l_1}\} \quad (14)$$

The progressive wave pressure $p_{f1}$ is found from the sum of Formulas (13) and (14), and the following Formula (15) is found by substituting that sum in and simplifying Formulas (11) and (13).

$$p_{f1} = \frac{p_{f3}}{4Z_{0A}Z_{0B}} \{(Z_{0A} + Z_{0B})^2 e^{(\gamma_A - \gamma_B)d} + (Z_{0A} - Z_{0B})^2 e^{-(\gamma_A + \gamma_B)d}\} \quad (15)$$

Formula (15) expresses a relationship between the progressive wave pressure $p_{f1}$ in the segment (0-1) and the progressive wave pressure $p_{f3}$ in the segment (2-3), and a transmission loss from point 0 to point 3 can be calculated from this relational expression. In other words, a transmission loss T from point 0 to point 3 can be expressed by the following Formula (16), using the energy ratio between the progressive waves at each point.

$$T = 10\log \frac{|p_{1f}|^2}{|p_{3f}|^2} \quad (16)$$

Substituting Formula (16) in Formula (15) results in the following Formula (17).

$$T = 10\log \left| \frac{1}{4Z_{0A}Z_{0B}}\{(Z_{0A} + Z_{0B})^2 e^{(\gamma_A - \gamma_B)d} + (Z_{0A} - Z_{0B})^2 e^{-(\gamma_A + \gamma_B)d}\} \right|^2 \quad (17)$$

A formula of a volume elasticity equivalent to a combination of a fluid and a tube wall in a viscoelastic tube, derived from the compliance of a thick viscoelastic tube, is introduced for a pulse wave propagation velocity c in the vascular pathway; an example can be found in Literature 1 (Hironori SATO, Yuji ISEKI, Hideo UTSUNO, Hiroshi MATSUHISA, Keisuke YAMADA, and Katsutoshi SAWADA, "Identification of pulse wave propagation characteristics in viscoelastic tube", Journal of the Japan Society of Mechanical Engineers, Series B, Vol. 76, No. 766 (2010), pp. 961-969). By substituting the volume elasticity formula, the pulse wave propagation velocity c in the vascular pathway is expressed by the following Formula (18).

$$c = \sqrt{\frac{E}{2(1+v)\rho} \cdot \frac{R_o^2 - R_i^2}{R_i^2(1-2v) + R_o^2}} \quad (18)$$

where E represents the Young's modulus;
$R_i$ represents the inner radius;
$R_o$ represents the outer radius; and
v represents Poison's ratio.

Here, when a pulse wave propagation velocity in the segment (1-2) serving as the middle section is represented by $c_A$ and a pulse wave propagation velocity in the segments (0-1) and (2-3) serving as the peripheral sections is represented by $C_B$, when the outer radius $R_o$ and the inner radius $R_i$ are replaced and the wall thickness is aggregated to the denominator, focusing on the ratio of wall thickness to inner radius results in the following Formulas (19) and (20).

$$c_A = \sqrt{\frac{E_A}{2(1+v)\rho} \cdot \frac{1}{1 + \frac{2(1-v)}{\frac{h_A}{R_A}\left(\frac{h_A}{R_A} + 2\right)}}} \quad (19)$$

$$c_B = \sqrt{\frac{E_B}{2(1+v)\rho} \cdot \frac{1}{1 + \frac{2(1-v)}{\frac{h_B}{R_B}\left(\frac{h_B}{R_B} + 2\right)}}} \quad (20)$$

Accordingly, with respect to an angular frequency ω, the propagation constant $\gamma_A$ of the middle section and the propagation constant $\gamma_B$ of the peripheral sections can be expressed by the following Formulas (21) and (22).

$$\gamma_A = j\frac{\omega}{c_A} = j\frac{\omega}{\sqrt{\frac{E_A}{2(1+v)\rho} \cdot \frac{1}{1 + \frac{2(1-v)}{\frac{h_A}{R_A}\left(\frac{h_A}{R_A} + 2\right)}}}} \quad (21)$$

$$\gamma_B = j\frac{\omega}{c_B} = j\frac{\omega}{\sqrt{\frac{E_B}{2(1+v)\rho} \cdot \frac{1}{1 + \frac{2(1-v)}{\frac{h_B}{R_B}\left(\frac{h_B}{R_B} + 2\right)}}}} \quad (22)$$

Meanwhile, the characteristic impedance $Z_0$ for the volumetric flow rate can be expressed by the following Formula (23) when a cross-sectional area is represented by S.

$$Z_0 = \frac{\rho c}{S} \quad (23)$$

When the characteristic impedance in the segment (1-2) serving as the middle section is represented by $Z_{0A}$ and the characteristic impedance in the segments (0-1) and (2-3) serving as the peripheral sections is represented by $Z_{0B}$, the following Formulas (24) and (25) can be derived using Formulas (19) and (20).

$$Z_{0A} = \frac{\rho c_A}{\pi R_A^2} \quad (24)$$

$$Z_{0B} = \frac{\rho c_B}{\pi R_B^2} \quad (25)$$

b3: Relationship between Shape of Middle Section and Transmission Loss

Next, the effect of changes in the shape (inner radius and length) of the middle section, which simulates an arterial aneurysm, will be considered. This refers to evaluating the relationship between the size of the arterial aneurysm and actually-observed pulse waves using the model, as will be described in detail later. Hereinafter, the effects on transmission loss when the inner radius $R_A$, Young's modulus $E_A$, and length d of the middle section are respectively changed will be considered.

i. Changes in Inner Radius $R_A$

First, changes in the inner radius $R_A$ will be considered. Here, to simplify the formula variation and the evaluation, $\alpha_R$ is introduced for a ratio of the inner radius $R_A$ of the middle section (the segment (1-2)) to the inner radius $R_B$ of the peripheral sections (the segments (0-1) and (2-3)). In other words, the ratio $\alpha_R$ can be expressed by the following Formula (26).

$$\alpha_R = \frac{R_A}{R_B} \quad (26)$$

At this time, assuming that a ratio $h_B/R_B$ of the wall thickness to the inner radius of the peripheral sections is equal to a ratio $h_A/R_A$ of the wall thickness to the inner radius of the middle section and that the ratios are constant, the pulse wave propagation velocities are also equal. In this case, Formula (24) can be varied using Formula (26) to obtain the following Formula (27).

$$Z_{0A} = \frac{\rho c_B}{\pi (\alpha_R R_B)^2} = \frac{1}{\alpha_R^2} Z_{0B} \quad (27)$$

Substituting these formulas in Formula (17) results in the following Formula (28).

$$T = 10 \log \left| \frac{1}{4 \frac{1}{\alpha_R^2} Z_{0B}^2} \left\{ \left( \frac{1}{\alpha_R^2} Z_{0B} + Z_{0B} \right)^2 e^{(\gamma_A - \gamma_B)d} + \left( \frac{1}{\alpha_R^2} Z_{0B} + Z_{0B} \right)^2 e^{-(\gamma_A + \gamma_B)d} \right\} \right|^2 \quad (28)$$

Furthermore, because the propagation constant $\gamma_B$ of the peripheral sections and the propagation constant $\gamma_A$ of the middle section are equal, the following Formula (29) can be derived.

$$T = 10 \log \left| \frac{\alpha_R^2}{4 Z_{0B}^2} \left\{ \left( \frac{1 + \alpha_R^2}{\alpha_R^2} Z_{0B} \right)^2 + \left( \frac{1 - \alpha_R^2}{\alpha_R^2} Z_{0B} \right)^2 e^{-2\gamma_B d} \right\} \right|^2 \quad (29)$$

Accordingly, in the case where the following Formula (30) holds true with respect to an integer m, the transmission loss T takes on a maximum value $T_{max}$.

$$\gamma_B d = -m\pi \quad (30)$$

The maximum value $T_{max}$ of the transmission loss T is expressed as indicated in the following Formula (31).

$$T_{max} = 10 \log \left| \frac{\alpha_R^4 + 1}{2\alpha_R^2} \right|^2 \quad (31)$$

The following characteristic behavior can be seen based on the above analysis.

(1) The maximum value of the transmission loss T increases as the ratio $\alpha_R$ of the middle section inner radius $R_A$ to the peripheral section inner radius $R_B$ increases.

(2) There is no effect on the transmission loss T in the case where the Young's modulus is the same between the peripheral sections and the middle section.

ii. Changes in Length d

Next, changes in the length d of the middle section, which simulates an arterial aneurysm, will be considered. Based on the aforementioned Formula (21), the length d has no effect on the propagation constant $\gamma_A$ of the middle section, and based on the aforementioned Formula (24), the length d also has no effect on the characteristic impedance $Z_{0A}$ of the middle section. Accordingly, the following Formula (32) can be derived by substituting Formula (22) in Formula (30) and solving for an angular frequency $\omega_f$.

$$\omega_f = -m\pi \frac{\sqrt{\frac{E_B}{2(1+v)\rho} \cdot \frac{1}{1 + \frac{2(1-v)}{\frac{h_B}{R_B}\left(\frac{h_B}{R_B} + 2\right)}}}}{jd} \quad (32)$$

That is, the transmission loss T takes on the maximum value with each angular frequency $\omega_f$ that fulfills Formula (32). Here, to simplify the formula variation and the evaluation, a frequency interval at which the transmission loss T takes on the maximum value will be referred to as a "fundamental frequency". This frequency interval (fundamental frequency) is determined by a ratio between the pulse wave propagation velocity $c_A$ and the length d.

iii. Changes in Young's Modulus

Next, changes in the Young's modulus will be considered. Here, to simplify the variation of the formula and the evaluation, $a_E$ is introduced for a ratio of the Young's modulus of the middle section (the segment (1-2)) to the Young's modulus of the peripheral sections (the segments (0-1) and (2-3)). In other words, the ratio $\alpha_E$ can be expressed by the following Formula (33).

$$\alpha_E = \frac{E_A}{E_B} \quad (33)$$

The following Formula (34) can be derived by substituting the Young's modulus ratio $\alpha_E$ in Formula (19).

$$c_A = \sqrt{\alpha_E}\sqrt{\frac{E_B}{2(1+v)\rho} \cdot \frac{1}{1 + \frac{2(1-v)}{\frac{h_B}{R_B}\left(\frac{h_B}{R_B}+2\right)}}} \quad (34)$$

Based on Formula (34), the pulse wave propagation velocity $c_A$ in the middle section can be expressed by the following Formula (35).

$$c_A = \sqrt{\alpha_E}c_B \quad (35)$$

Likewise, based on Formula (24), the characteristic impedance $Z_{0A}$ in the middle section can be expressed by the following Formula (36).

$$Z_{0A} = \sqrt{\alpha_E}Z_{0B} \quad (36)$$

Furthermore, the following Formula (37) can be derived from Formula (21).

$$\gamma_A = j\frac{\omega}{\sqrt{\alpha_E}\,c_B} = \frac{1}{\sqrt{\alpha_E}}\gamma_B \quad (37)$$

The square root of the ratio of the Young's modulus in the middle section to the Young's modulus in the peripheral sections is equal to the ratios of the pulse wave propagation velocities and characteristic impedances in the peripheral sections and the middle section. When these are substituted in Formula (17), the transmission loss T can be expressed by the following Formula (38).

$$T = 10 \log \left| \frac{1}{4\sqrt{\alpha_E}} \left\{ (\sqrt{\alpha_E}+1)^2 e^{\gamma_B d\left(\frac{1}{\sqrt{\alpha_E}}-1\right)} + (\sqrt{\alpha_E}-1)^2 e^{-\gamma_B d\left(\frac{1}{\sqrt{\alpha_E}}+1\right)} \right\} \right|^2 \quad (38)$$

From Formula (38), it can be seen that the pulse wave propagation velocity increases as the ratio of the Young's modulus in the middle section to the Young's modulus in the peripheral sections increases, and that the fundamental frequency of the transmission loss also increases along therewith. It can also be seen that the characteristic impedance increases as the ratio of the Young's modulus in the middle section to the Young's modulus in the peripheral sections increases, and that a reflection coefficient at the borders decreases along therewith; the transmission loss decreases as a result.

b4: Verification Result i. Transmission Loss Simulation

Next, changes in the transmission loss produced when a pulse wave traverses an arterial aneurysm will be considered based on the aforementioned formulas expressing the transmission loss T. Transmission losses for the pressures $p_0$ and $p_3$ between point 0 and point 3 are calculated through the aforementioned Formula (17), and the effect thereof on pulse wave propagation is found. Here, an aortic aneurysm occurring the abdominal area is assumed, and the data shown in the following Table 1 is employed as values near the abdominal aorta.

TABLE 1

Basic Parameters of Simplified Model of Aortic Aneurysm

| | | |
|---|---|---|
| Length (m) | $l_1$ | 0.05 |
| | $l_2$ | 0.10 |
| | $l_3$ | 0.05 |
| Young's modulus (MPa) | $E_A$ | 0.4 |
| | $E_B$ | 0.4 |
| Outer radius (m) | $R_{Ao}$ | 0.036 |
| | $R_{Bo}$ | 0.018 |
| Inner radius (m) | $R_A$ | 0.020 |
| | $R_B$ | 0.010 |
| Density of blood (kg/m³) | $\rho$ | 1050 |
| Poison's ratio | $v$ | 0.3 |

Figure 3:
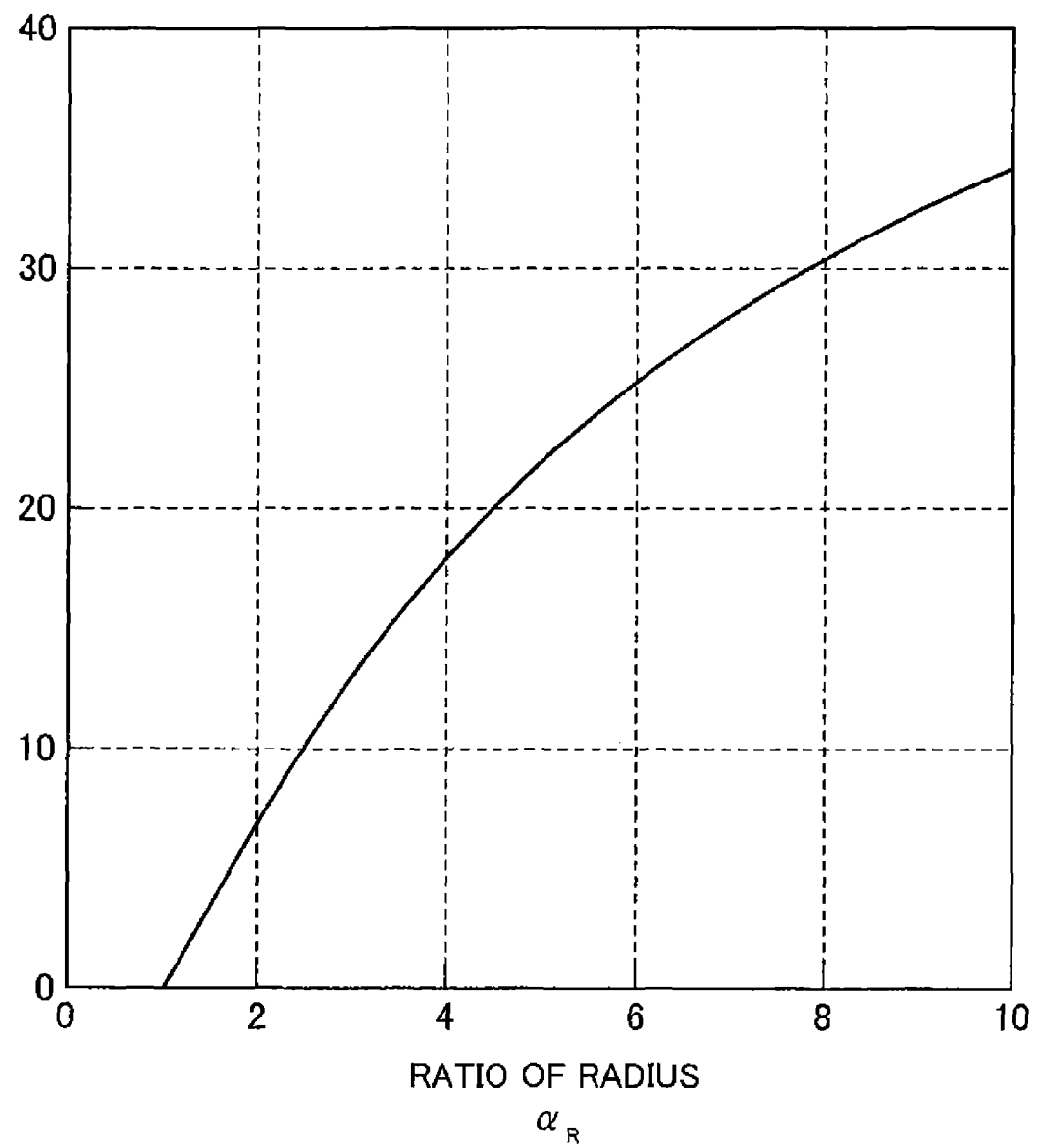
FIG. 3 is a diagram illustrating a result of evaluating the effect of an inner radius of a middle section, calculated according to a transmission loss calculation formula according to the embodiment.

First, effects of the inner radius of the middle section (the segment (1-2)) will be considered. FIGS. 2 and 3 are diagrams illustrating results of evaluating the effect of the inner radius of the middle section, calculated according to the transmission loss calculation formula according to the present embodiment.

FIG. 2 illustrates changes in the transmission loss (frequency characteristics) when the inner radius of the middle section is changed while keeping the other parameters and the wall thickness constant. FIG. 3 is a diagram illustrating changes in the transmission loss using the ratio $\alpha_R$ of the inner radius of the middle section to the inner radius of the peripheral section as a parameter, based on the aforementioned Formula (31).

Based on FIG. 2 and FIG. 3, it can be seen that the transmission loss T increases due to an increase in the ratio $\alpha_R$ of the inner radius of the middle section to the inner radius of the peripheral sections. Meanwhile, it can be seen that the ratio $\alpha_R$ has no effect on the fundamental frequency of the transmission loss T.

Figure 4:
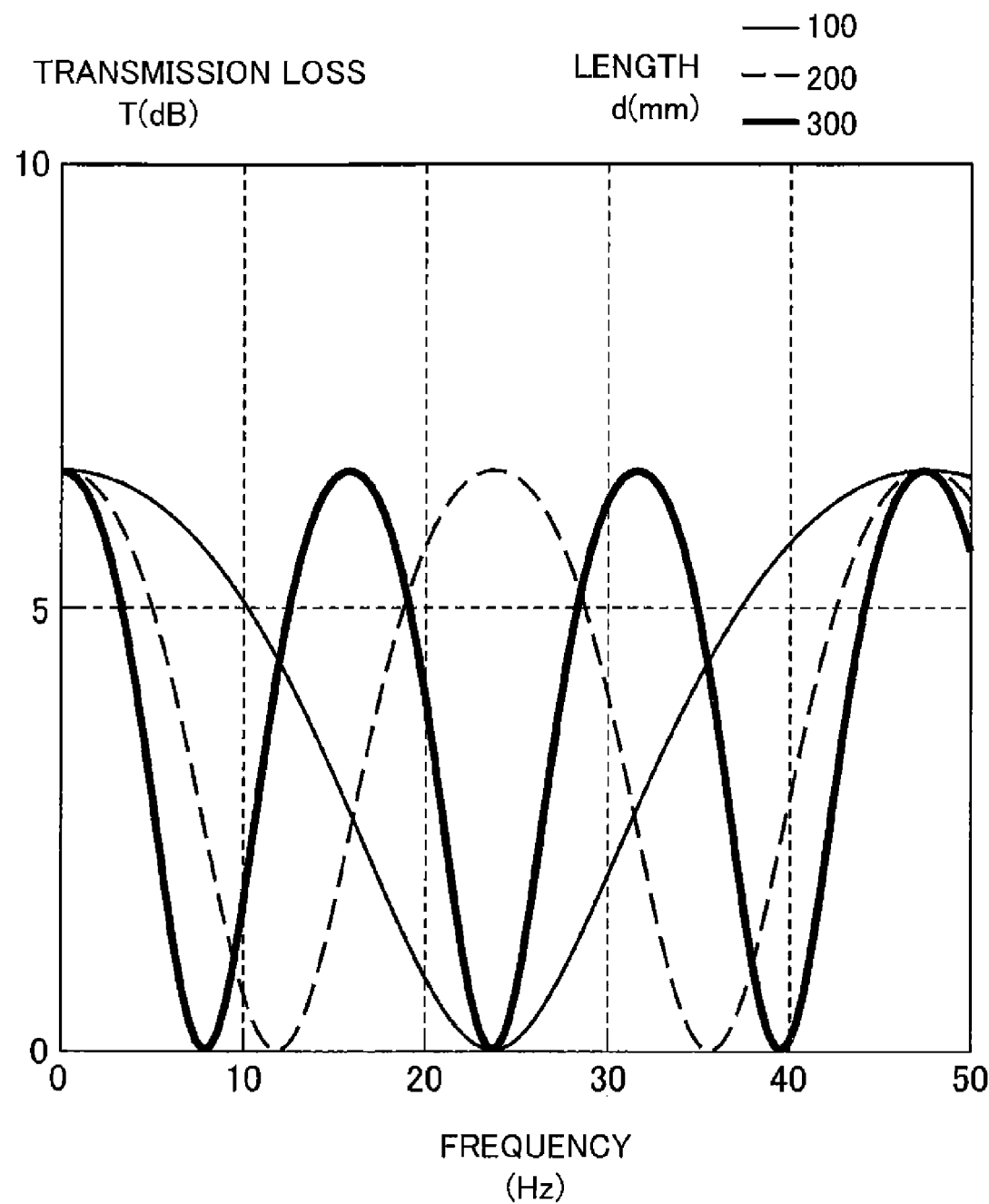
FIG. 4 is a diagram illustrating a result of evaluating the effect of a length of a middle section, calculated according to a transmission loss calculation formula according to the embodiment.
Figure 5:
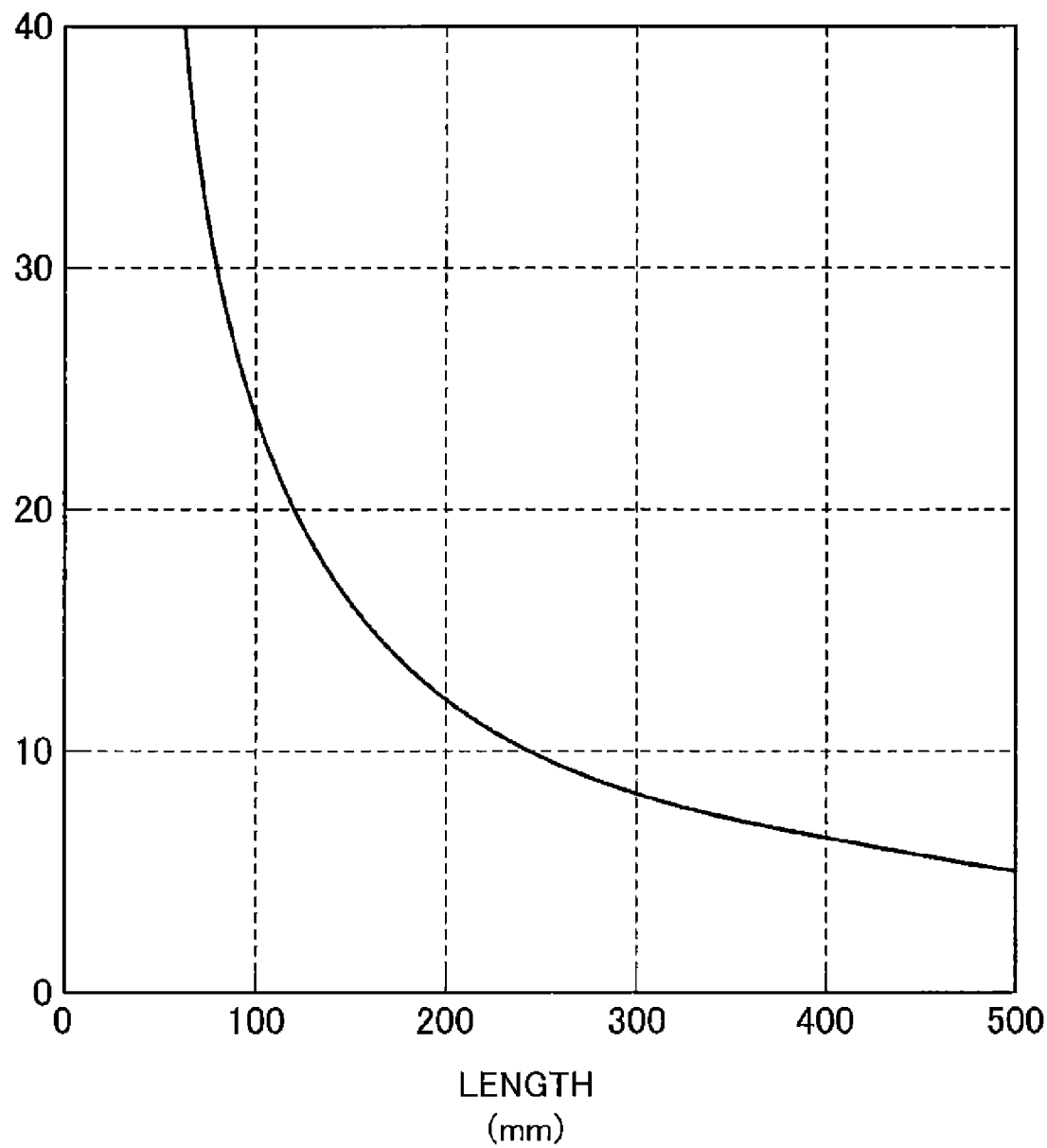
FIG. 5 is a diagram illustrating a result of evaluating the effect of a length of a middle section, calculated according to a transmission loss calculation formula according to the embodiment.

Next, effects of the length of the middle section (the segment (1-2)) will be considered. FIGS. 4 and 5 are diagrams illustrating results of evaluating the effect of the length of the middle section, calculated according to the transmission loss calculation formula according to the present embodiment. The inner radius $R_A$ of the middle section is fixed at 20 mm in the evaluation results shown in FIGS. 4 and 5.

FIG. 4 illustrates changes in the transmission loss (frequency characteristics) at the pressures $p_0$ and $p_3$ between point 0 and point 3 when the length d of the middle section is changed, with the inner radius $R_A$ of the middle section fixed at 20 mm. FIG. 5 illustrates a relationship between the length d of the middle section and the frequency interval (fundamental frequency) at a minimum value, based on the aforementioned Formula (32).

In FIGS. 4 and 5, it can be seen that the fundamental frequency decreases as the length of the middle section (the tube) increases. On the other hand, it can be seen that the length of the middle section has no effect on the transmission loss T.

Figure 6:
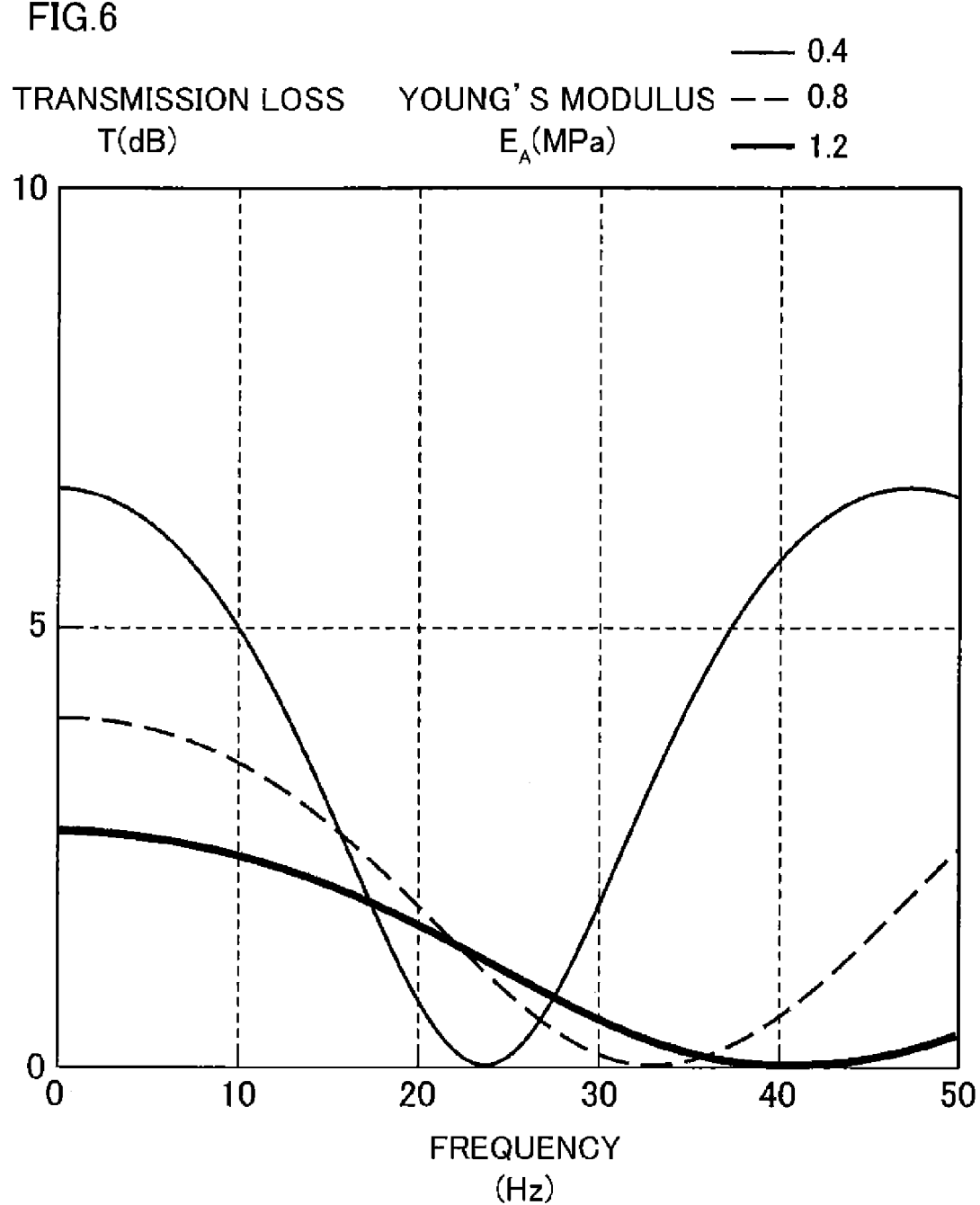
FIG. 6 is a diagram illustrating a result of evaluating the effect of the Young's modulus of a middle section, calculated according to a transmission loss calculation formula according to the embodiment.
Figure 7:
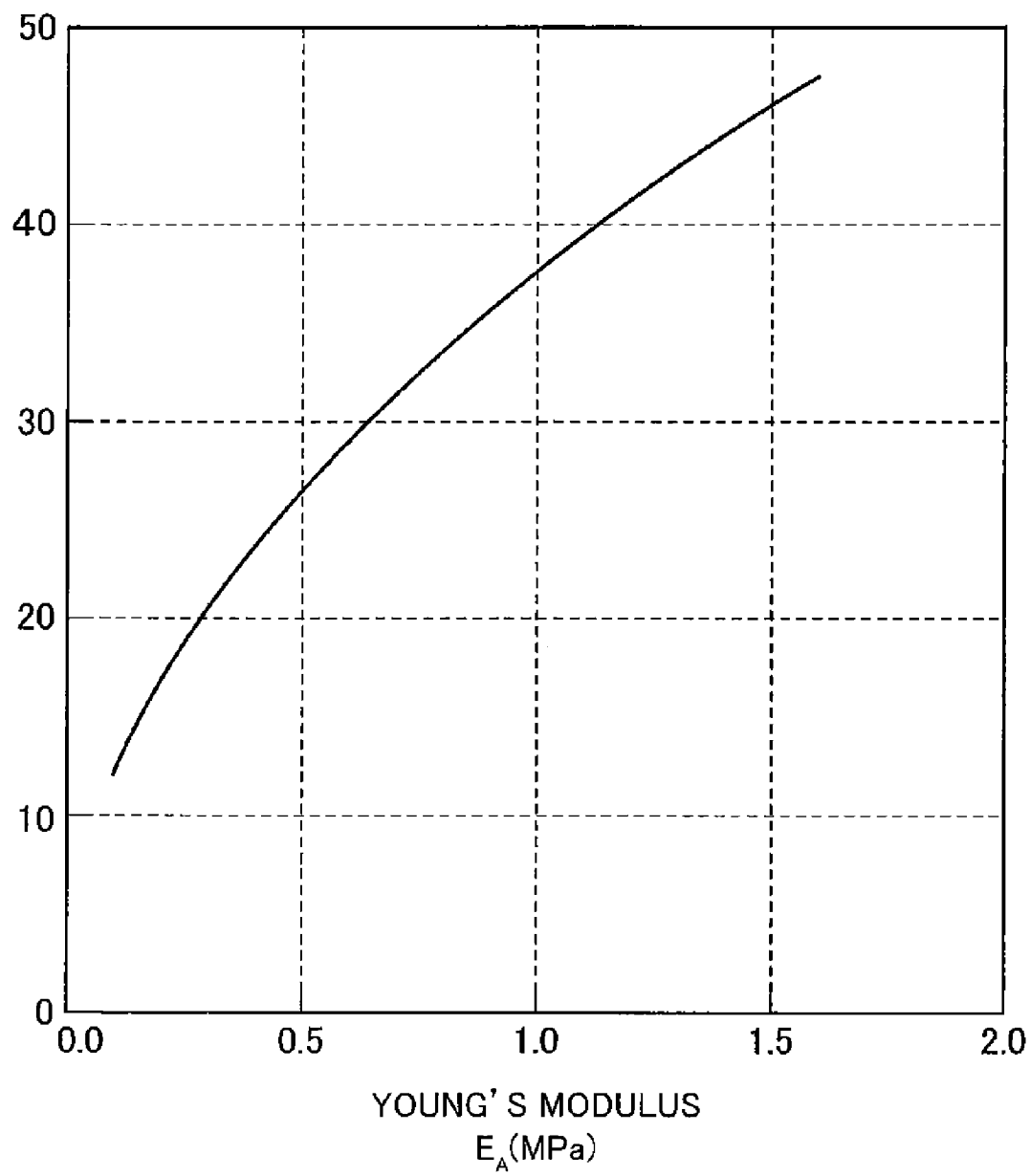
FIG. 7 is a diagram illustrating a result of evaluating the effect of the Young's modulus of a middle section, calculated according to a transmission loss calculation formula according to the embodiment.

Next, effects of the Young's modulus of the middle section (the segment (1-2)) will be considered. FIGS. 6 and 7 are diagrams illustrating results of evaluating the effect of the Young's modulus of the middle section, calculated according to the transmission loss calculation formula according to the present embodiment. The inner radius $R_A$ of the middle section is fixed at 20 mm in the evaluation results shown in FIGS. 6 and 7.

FIG. 6 illustrates changes in the transmission loss (frequency characteristics) at the pressures $p_0$ and $p_3$ between point 0 and point 3 when the Young's modulus $E_A$ of the middle section is changed, with the inner radius $R_A$ of the middle section fixed at 20 mm. FIG. 7 illustrates a relationship between the Young's modulus $E_A$ of the middle section and the frequency interval (fundamental frequency) at a minimum value, based on the aforementioned Formula (38).

Based on FIG. 6 and FIG. 7, it can be seen that the transmission loss T decreases due to an increase in the Young's modulus of the middle section. Furthermore, it can be seen that the fundamental frequency is proportional to the square root of the Young's modulus of the middle section.

ii. Simulation Using Pulse Wave Propagation Model of Human Arterial System

Next, characteristics appearing in the aforementioned transfer function will be considered using a pulse wave propagation model of the human arterial system. More specifically, it will be confirmed that an arterial aneurysm can be detected even in the case where the effects of blood vessel walls and blood thickness, the effect of tapering of blood vessel diameters, the effect of branching and peripheral blood vessels, and the effect of transfer function measurement points are included.

Figure 8:
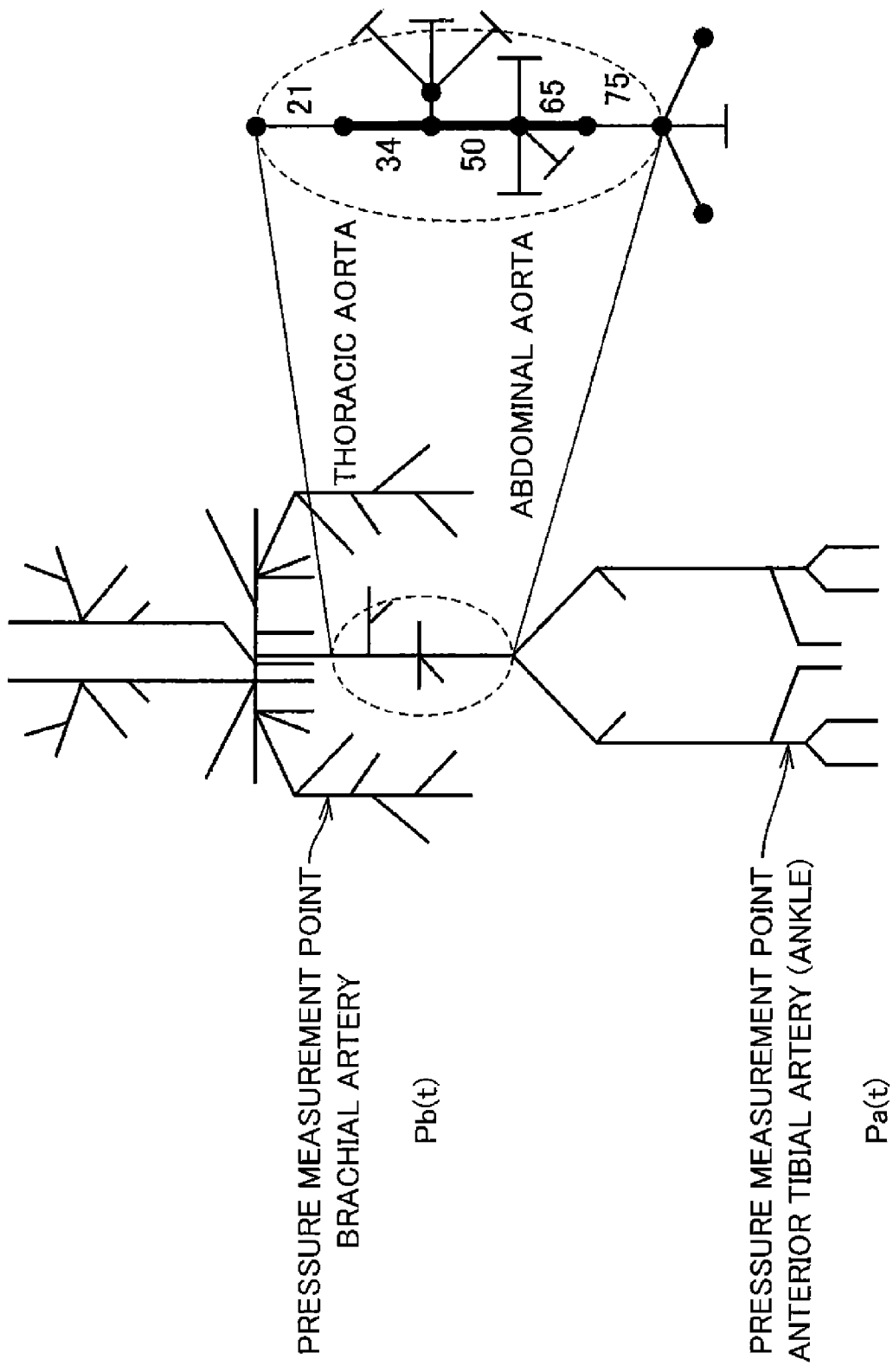
FIG. 8 is a schematic diagram illustrating a pulse wave propagation model of the human arterial system.

FIG. 8 is a schematic diagram illustrating a pulse wave propagation model of the human arterial system. The pulse wave propagation model of the human arterial system shown in FIG. 8 is based on Literature 2 (Avolio, A. P., "Multi-branched model of human arterial system", Medical and Biological Engineering and Computing, Vol. 18 (1980), pp. 709-718), Literature 3 (Hironori SATO, Yuji ISEKI, Hideo UTSUNO, Hiroshi MATSUHISA, Keisuke YAMADA, and Katsutoshi SAWADA, "An Elaborated Multi-branched Model of Human Arteries", Journal of the Japan Society of Mechanical Engineers, Series C, 77(779) (2011), pp. 2695-2710), and so on.

To confirm the effects of arterial aneurysms on pulse wave propagation, aortic aneurysms in abdominal areas having different lengths d were considered. More specifically, three aortic aneurysms were considered, as shown in the following Table 2. The "segment numbers" in Table 2 indicate numbers where an aortic aneurysm is present. For example, the case where the segment numbers are "50" and "65" indicates that an aortic aneurysm is present in the segments numbered "50" and "65" in the pulse wave propagation model of the human arterial system illustrated in FIG. 8.

TABLE 2

Sets of Segments of Simulated Aortic Aneurysms and Parameters thereof

| Case | Segment Number | Inner Radius R (mm) | Length d (mm) | Wall Thickness h (mm) | Young's modulus $E_A$ (MPa) |
|---|---|---|---|---|---|
| (1) | 65 | 5.7 | 53 | 0.8 | 0.4 |
| (2) | 50, 65 | 9.5, 5.7 | 105 | 0.8 | 0.4 |
| (3) | 34, 50, 65 | 9.5, 9.5, 5.7 | 157 | 0.8 | 0.4 |

In each example shown in Table 2, the pulse wave transfer function $P_A/P_B$ between the upper extremities and the lower extremities was calculated having changed the inner radius R, the length d, and the overall Young's modulus. The transfer function $P_A/P_B$ can be defined as indicated by the following Formula (39), using Fourier signals Pa(f) and Pb(f) obtained by performing Fourier transforms (frequency transforms) on measurement signals Pa(t) and Pb(t), which are pulse wave signals.

$$\frac{P_A}{P_B} = \frac{P_b^*(f)P_a(f)}{P_b^*(f)P_b(f)} \quad (39)$$

Here, $P_b^*(f)$ is a complex conjugate of $P_b(f)$.

Typically, pulse waves in the upper extremities and the lower extremities can be obtained by attaching a given detection device to a brachial artery and an anterior tibial artery. That is, pulse waves in the lower extremities are detected at a measurement location in the vascular pathway from the measurement subject's heart to an area where an arterial aneurysm is predicted to occur, whereas pulse waves in the upper extremities are detected at a measurement location in the vascular pathway from the measurement subject's heart to an area that is different from the area where an arterial aneurysm is predicted to occur.

Figure 9A:
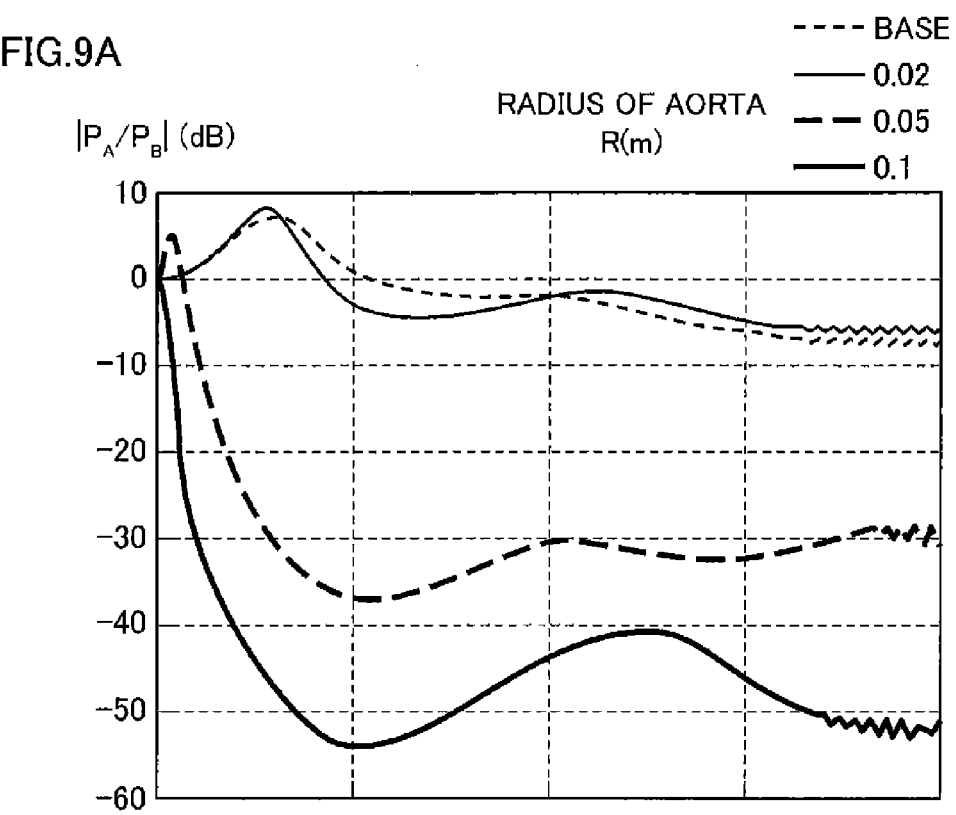
FIG. 9 is a gain diagram and a phase diagram for a transfer function $P_A/P_B$ when an inner radius R of an abdominal aorta at segment number 65 is varied.
Figure 9B:
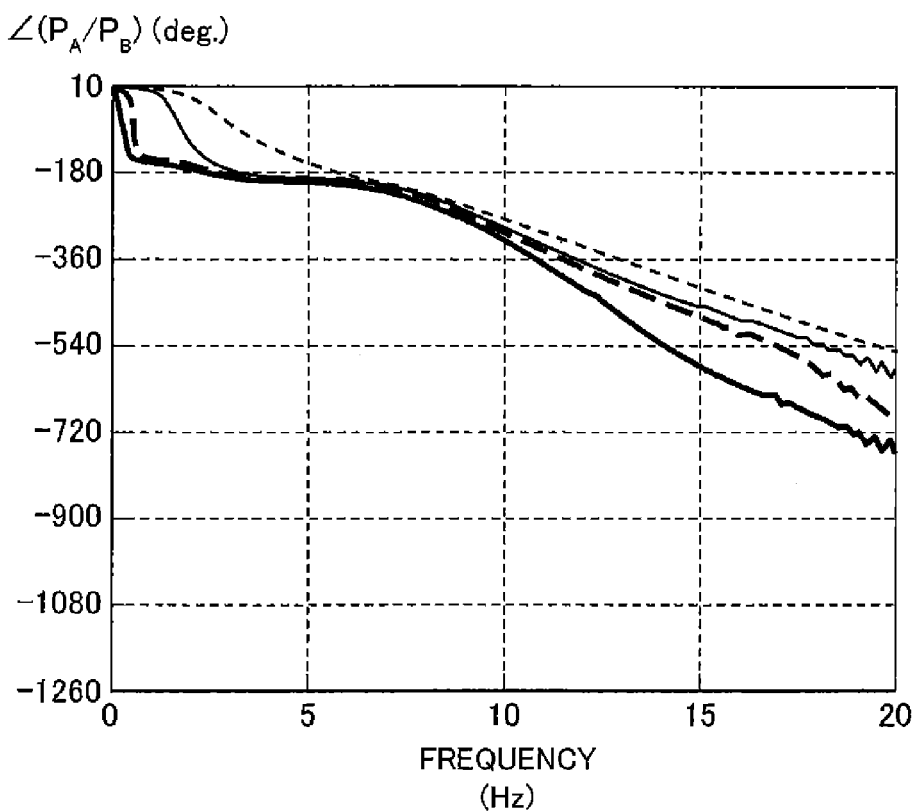
Figure 10A:
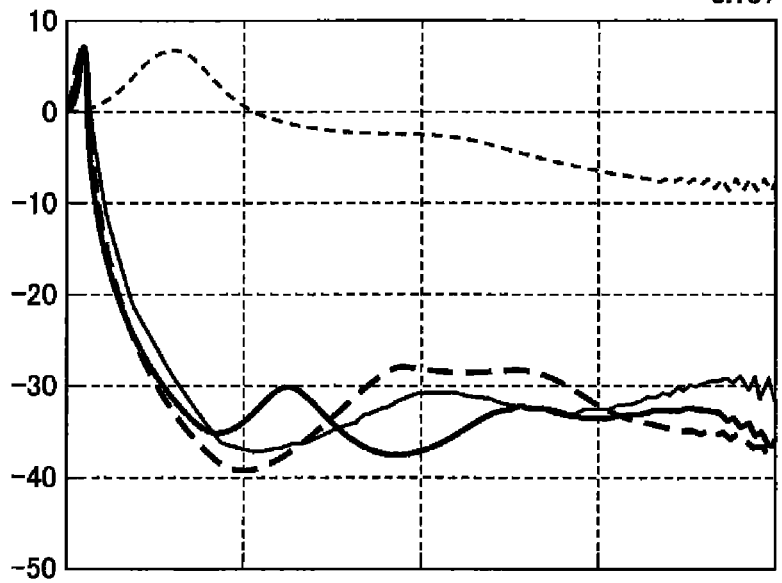
FIG. 10 is a gain diagram and a phase diagram for a transfer function $P_A/P_B$ when the inner radius of the arterial aneurysm is fixed at 50 mm and the length thereof is sequentially increased.
Figure 10B:
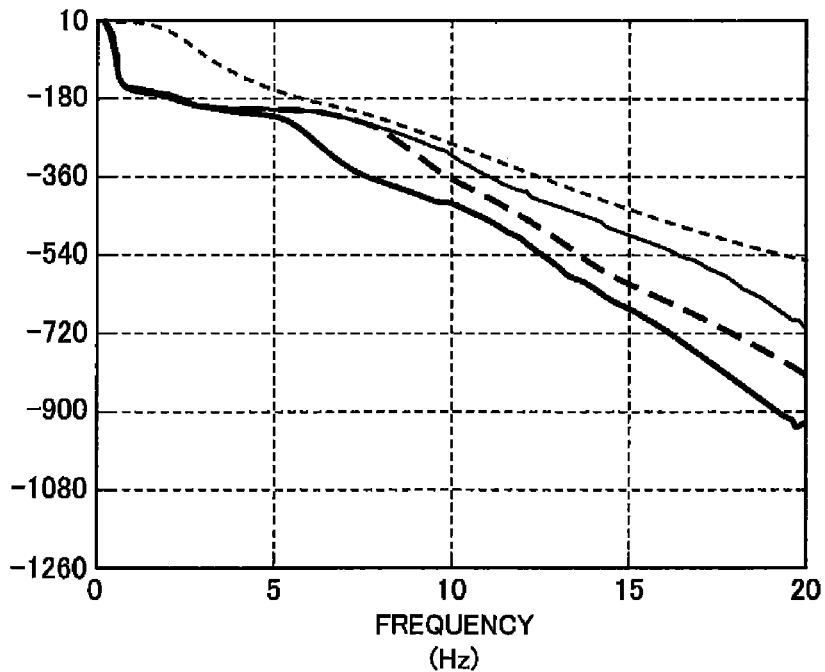

FIGS. 9 to 11 are diagrams illustrating results of the transfer functions obtained through simulations using the pulse wave propagation model of the human arterial system.

FIG. 9 is a gain diagram and a phase diagram for the transfer function $P_A/P_B$ when the inner radius R of the abdominal aorta at segment number 65 is varied. In FIG. 9, "base" refers to a case where the inner radius R of the abdominal aorta is set to 5.7 mm as specified in the pulse wave propagation model of the human arterial system. In other words, this corresponds to a state where no aortic aneurysm is present.

As shown in FIG. 9, the gain of the transfer function $P_A/P_B$ drops as the inner radius R increases. This matches the increase in the transmission loss T as the ratio of the inner radius in the middle section (a distended section) to the inner radius of the peripheral sections increases.

FIG. 10 is a gain diagram and a phase diagram for the transfer function $P_A/P_B$ when the inner radius of the arterial aneurysm is fixed at 50 mm and the length thereof is sequentially increased. More specifically, starting with a state in which an arterial aneurysm is present only in the abdominal aorta indicated by segment number 65, the length d of the middle section (the distended section) was varied by sequentially extending the range in which the arterial aneurysm to the abdominal aorta at segment number 50 and to the thoracic aorta at segment number 34, as indicated by cases (1) to (3) in Table 2. In FIG. 10, "base" refers to the case where the length d of the middle section (the distended section) is "0". In other words, this corresponds to a state where no aortic aneurysm is present.

As shown in FIG. 10, the fundamental frequency decreases (narrows) in proportion to the length d of the middle section (the distended section), but there is no change in the transmission loss. Furthermore, it can be seen in the phase diagram that the phase changes by 180 degrees with each fundamental frequency.

FIG. 11 is a gain diagram and phase diagram for the transfer function $P_A/P_B$ when the inner radius of the arterial aneurysm is fixed at 50 mm and the overall Young's modulus is varied. More specifically, the inner radii of the abdominal aorta at segment numbers 50 and 65 are both fixed at 50 mm, and the overall Young's modulus is changed to 1, 2, and 3×. In FIG. 11, "base" refers to a state where no aortic aneurysm is present.

As shown in FIG. 11, increasing the Young's modulus increases the pulse wave propagation velocity, and the fundamental frequency increases (widens) as a result; however, there is no change in the maximum value and minimum value of the transmission loss.

b5: Conclusion

Based on the aforementioned analytical approach, it can be said that the following points can be focused on in order to detect an arterial aneurysm.

The transmission loss T increases as the ratio $\alpha_R$ of the inner radius of the middle section to the inner radius of the peripheral sections increases.

Although the transmission loss T decreases as the ratio $\alpha_E$ of the Young's modulus of the middle section to the Young's modulus of the peripheral sections increases, the transmission loss T is not affected by the overall Young's modulus.

The fundamental frequency, which is a frequency interval in which extreme values (maximum value/minimum value) are found, is in an inverse proportion to the length d of the arterial aneurysm.

The fundamental frequency is determined by the ratio between the pulse wave propagation velocity and the length of the arterial aneurysm.

Accordingly, the presence of an arterial aneurysm can be estimated based on the magnitude of the transmission loss T and the fundamental frequency, whereas the size of the arterial aneurysm (the inner diameter and the length thereof) can be estimated by measuring the overall Young's modulus.

In the present embodiment, in order to simplify the detection device and the detection method, pulse wave signals are detected at each of two measurement points in the arteries of a measurement subject and at least one of the presence/absence and the size of an arterial aneurysm is detected by comparing the frequency characteristics between the detected pulse wave signals.

It is preferable for the pulse wave signals to be detected at a measurement location in the vascular pathway from the measurement subject's heart to an area where an arterial aneurysm is predicted to occur (typically, the anterior tibial artery) and at a measurement location in the vascular pathway from the measurement subject's heart to an area that is different from the area where an arterial aneurysm is predicted to occur (typically, a brachial artery), respectively. This is because the presence/absence and size of the arterial aneurysm can be more correctly detected by ensuring that one of the detected pulse wave signals is not being affected by the arterial aneurysm. Using such pulse wave signals is particularly useful when detecting aortic aneurysms in the abdominal area, the chest area, and so on.

More specifically, in the present embodiment, transfer functions are calculated from the respective pulse wave signals and the presence/absence and size of an arterial aneurysm is detected based on the calculated transfer functions, for the following purposes.

1. Estimating the inner diameter of the arterial aneurysm based on the gain (amplitude) ratio between the transfer functions.

2. Estimating the length of the arterial aneurysm based on the frequency interval (fundamental frequency) at which the gain (amplitude) of the transfer functions takes on extreme values (maximum value/minimum value). Here, a phase change in the transfer function corresponds to the fundamental frequency.

3. The accuracy at which the length of the arterial aneurysm is estimated can be improved by measuring the pulse wave propagation velocity at healthy areas where no arterial aneurysm is thought to be present (for example, between the heart and the carotid artery or the like).

C. Device Configuration

Next, a specific device configuration for detecting the presence/absence and/or size of an arterial aneurysm in a measurement subject will be described, based on the aforementioned analytical considerations.

Figure 12:
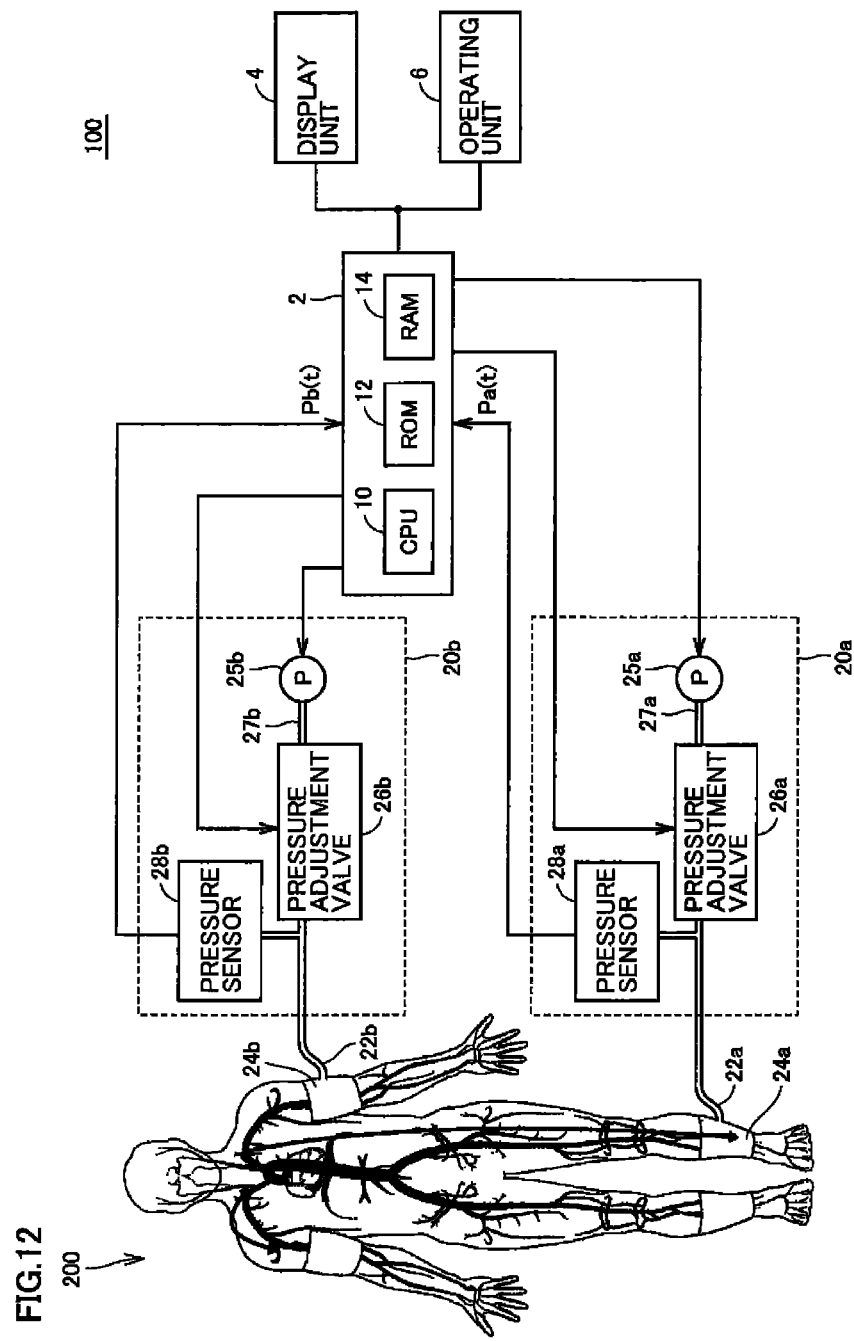
FIG. 12 is a general block diagram illustrating a measurement device according to an embodiment of the present invention.

FIG. 12 is a general block diagram illustrating a measurement device 100 according to an embodiment of the present invention.

As shown in FIG. 12, the measurement device 100 includes a processing unit 2, a display unit 4, an operating unit 6, and measurement units 20a and 20b.

The processing unit 2 is a unit that controls the measurement device 100 as a whole, and is generally configured of a computer including a CPU (central processing unit) 10, a ROM (read-only memory) 12, and a RAM (random access memory) 14.

The CPU 10 corresponds to a central processing unit that reads out programs stored in advance in the ROM 12 and executes those programs while using the RAM 14 as a working memory.

The display unit 4 and the operating unit 6 are connected to the processing unit 2. The display unit 4 prompts a user to input various types of settings, displays results of computations performed by the processing unit 2, and so on. In response to this, the user operates the operating unit 6 while confirming the content displayed in the display unit 4, and performs desired setting inputs, operations, and so on. Note that the display unit 4 is configured of, for example, an LED (light-emitting diode) display, an LCD (liquid-crystal display), or the like.

To be more specific, the processing unit 2 supplies measurement instructions to the measurement units 20a and 20b, receives the measurement signals Pa(t) and Pb(t) taken in response to the measurement instructions, and executes processing according to the present embodiment, which will be described later, based on the measurement signals Pa(t) and Pb(t).

The measurement units 20a and 20b measure time waveforms of pulse waves at predetermined measurement areas of a measurement subject 200 by increasing the internal pressure (called "cuff pressure" hereinafter) of pressure cuffs (air bladders) 24a and 24b worn on the respective measurement areas. In other words, the measurement signals Pa(t) and Pb(t) are pulse wave signals from the areas where the pressure cuffs 24a and 24b are respectively attached. As will be described later, the processing unit 2 executes processing using the frequency characteristics between the measurement signal Pa(t) and the measurement signal Pb(t), and thus the processing unit 2 supplies the measurement instructions simultaneously so that the measurement units 20a and 20b can measure the measurement signals in synchronization with each other.

To be more specific, the pressure cuffs 24a and 24b are attached to, for example, an ankle area (and preferably, the periphery of the anterior tibial artery) and an upper arm area (and preferably, the periphery of the brachial artery) of the measurement subject 200, and are inflated by air supplied from the measurement units 20a and 20b via tubes 22a and 22b, respectively. Due to this inflation, the measurement areas corresponding to the pressure cuffs 24a and 24b are pressurized, and pressure changes resulting from pulse waves at the measurement areas are transmitted to the measurement units 20a and 20b via the tubes 22a and 22b.

The measurement units 20a and 20b measure time waveforms of the pulse waves at the measurement areas by detecting these transmitted pressure changes. Note that it is preferable for computational processes to be carried out on a predetermined frequency component (for example, 0-20 Hz) of the measurement signals Pa(t) and Pb(t), and thus it is preferable for a measurement cycle (sampling cycle) of the measurement signals Pa(t) and Pb(t) to be shorter than a time interval based on that frequency component (for example, 25 ms).

In order to execute such measurement processes, the measurement unit 20a includes a pressure sensor 28a, a pressure adjustment valve 26a, a pressure pump 25a, and a tube 27a. The pressure sensor 28a is a detection section for detecting pressure fluctuations transmitted via the tube 22a. For example, the pressure sensor 28a includes a plurality of sensor elements arranged at predetermined intervals upon a semiconductor chip formed of single-crystal silicon or the like. The pressure adjustment valve 26a is provided between the pressure pump 25a and the pressure cuff 24a, and maintains a pressure used to inflate the pressure cuff 24a during measurement in a predetermined range. The pressure pump 25a operates in response to the measurement instruction from the processing unit 2, and supplies inflation air for inflating the pressure cuff 24a.

Likewise, the measurement unit 20b includes a pressure sensor 28b, a pressure adjustment valve 26b, a pressure pump 25b, and a tube 27b. The configurations of the respective units are the same as those of the measurement unit 20a.

Although the present embodiment describes a configuration in which pulse wave signals serving as biological signals are obtained by measuring pressure changes caused by pulse waves using pressure cuffs, for example, an extremely low constant current may be applied to the measurement areas of the measurement subject 200 and voltage changes arising due to changes in an impedance (a body impedance) produced when pulse waves are transmitted may be obtained as the pulse wave signals instead.

D. Arterial Aneurysm Determination Logic
First Embodiment
d1. Overview

The first embodiment will describe a configuration in which a transfer function is calculated for pressures between a measurement location where the pressure cuff 24a is attached (a measurement location in the vascular pathway from the measurement subject's heart to an area where an arterial aneurysm is predicted to occur) and a measurement location where the pressure cuff 24b is attached (a measurement location in the vascular pathway from the measurement subject's heart to an area that is different from the area where an arterial aneurysm is predicted to occur) from the respective pulse wave signals, and the presence/absence and/or size of an arterial aneurysm is detected using the calculated transfer function. In the first embodiment, the presence/absence of an arterial aneurysm is detected using a degree of variation in phase difference characteristics related to the transfer function. As described above, in the phase diagram for the transfer function, the phase changes by 180 degrees with each fundamental frequency. Thus this phase appears with greater frequency in the case where the fundamental frequency is low (narrow). Furthermore, because the fundamental frequency is in an inverse proportion with the length of the arterial aneurysm, there is a higher likelihood that an arterial aneurysm is present in cases where the fundamental frequency is relatively low (narrow). Accordingly, the presence of an arterial aneurysm can be determined with a higher level of certainty the greater the degree of variation is.

More specifically, in the first embodiment, phase difference characteristics ($\angle(P_A/P_B)$) of the transfer function $P_A/P_B$ are calculated by calculating the phase characteristics of the measurement signals Pa(t) and Pb(t) by performing frequency transforms thereon, and furthermore calculating phase differences at each frequency. Note that for the sake of simplicity, descriptions will be given using phase characteristics $\Phi a(f)$ and $\Phi b(f)$, which can be defined through the following Formula (40) using the respective Fourier signals Pa(f) and Pb(f).

$$\Phi_a(f)=\angle P_a(f)$$

$$\Phi_b(f)=\angle P_b(f) \qquad (40)$$

Then, it can be determined whether or not an arterial aneurysm is present in the vascular pathway in question based on the degree of variation in the phases found in the phase difference characteristics related to the calculated transfer functions. An example of a specific configuration for implementing such processing will be described hereinafter.

d2. Functional Configuration

Figure 13:
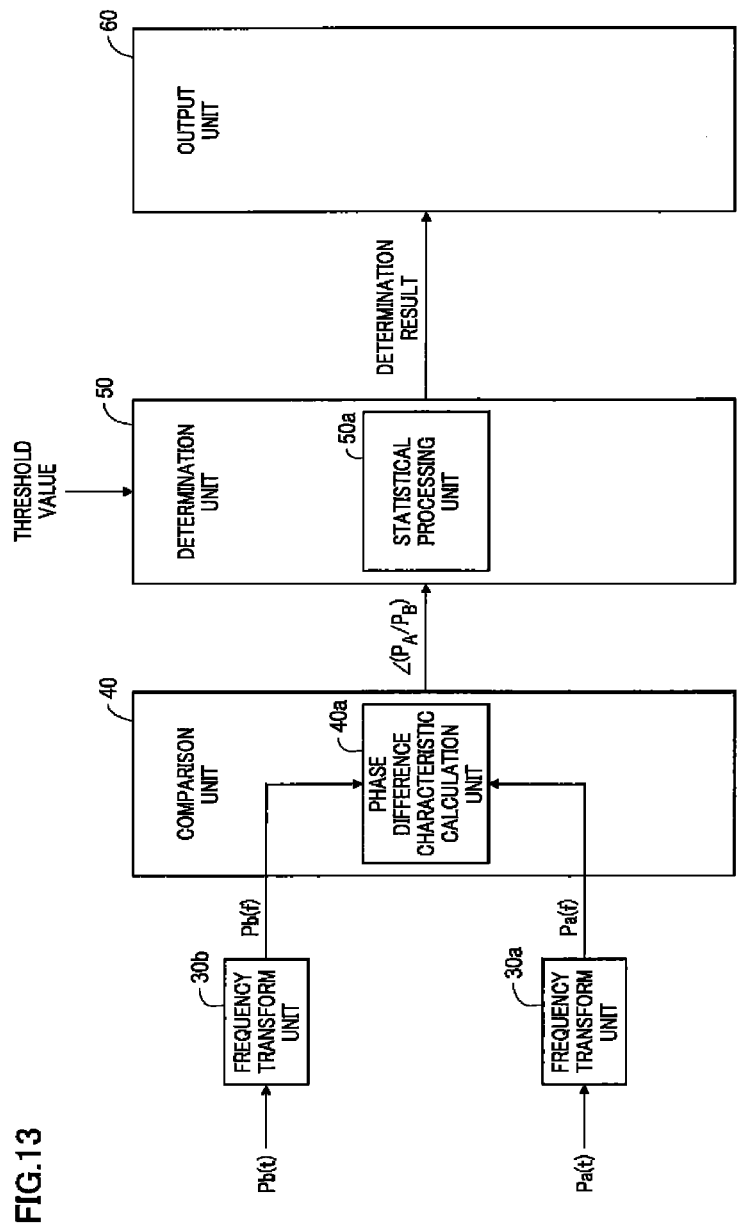
FIG. 13 is a schematic diagram illustrating functional blocks that implement processes for detecting an arterial aneurysm according to a first embodiment.

FIG. 13 is a schematic diagram illustrating functional blocks that implement processes for detecting an arterial aneurysm according to the first embodiment. Typically, the functional blocks illustrated in FIG. 13 are realized by the CPU 10 of the processing unit 2 (see FIG. 12) executing computational processes in accordance with a program stored in advance in the ROM 12 or the like.

As shown in FIG. 13, the processing unit 2 according to the first embodiment includes frequency transform units 30a and 30b, a comparison unit 40, a determination unit 50, and an output unit 60.

The frequency transform units 30a and 30b receive the measurement signals Pa(t) and Pb(t), which are time waveforms, over a predetermined period, and transform the received measurement signals Pa(t) and Pb(t) into frequency domain information. Generally, the frequency transform units 30a and 30b carry out the frequency transforms using fast Fourier transforms (FFT). Note that the embodiment is not limited to fast Fourier transforms, and any transform algorithm may be used as long as it transforms a time-domain signal into a frequency-domain signal such as a Fourier series.

In the first embodiment, the frequency transform units 30a and 30b output the phase characteristics $\Phi a(f)$ and $\Phi b(f)$ as the frequency-domain information. More specifically, the frequency transform unit 30a calculates the phase characteristics $\Phi a(f)$ indicating a phase for each frequency component in the measurement signal Pa(t), and outputs the calculated phase characteristic $\Phi a(f)$ to the comparison unit 40. Likewise, the frequency transform unit 30b calculates the phase characteristics $\Phi b(f)$ indicating a phase for each frequency component in the measurement signal Pb(t), and outputs the calculated phase characteristic $\Phi b(f)$ to the comparison unit 40.

The comparison unit 40 calculates phase differences in each frequency as comparison results, by comparing the frequency characteristics (in the first embodiment, phase difference characteristics) between the measurement signals Pa(t) and Pb(t), which are pulse wave signals. To be more specific, the comparison unit 40 includes a phase difference characteristic calculation unit 40a. The phase difference characteristic calculation unit 40a calculates the phase difference characteristics, indicating phase differences for each frequency, by calculating the difference between the phase characteristics Φa(f) and the phase characteristics Φb(f) for each frequency (phase characteristics Φa(f)—phase characteristics Φb(f)).

Note that when the phase differences between the measurement signal Pa(t) and the measurement signal Pb(t) at each frequency component are plotted, the phase diagram has discontinuous points with a ±180° boundary. This indicates that a phase difference greater than or equal to one cycle(360°) is present in frequency components greater than or equal to a predetermined frequency. Accordingly, the phase difference characteristic calculation unit 40a calculates actual phase difference characteristics after correcting the discontinuous points in the phase diagram with a unit (n×360°) equivalent to one or two or more cycles.

The phase difference characteristic calculation unit 40a plots a phase difference $A_i$ for a frequency $f_i$, corresponding to differences between the phase characteristics Φa(f) and the phase characteristics Φb(f), on the phase diagram. Note that the frequency $f_i$ is the ith frequency component, counting from the low-frequency side. By correcting the discontinuous points in the phase diagram as described above, the phase diagram that is plotted becomes continuous. The phase difference characteristic calculation unit 40a calculates a regression line using the phase differences $A_i$ that have been plotted on the phase diagram. The slope of the regression line (deg/Hz) corresponds to a phase line characteristic. Using an angle φ that corresponds to an amount of change in the phase difference characteristics with respect to the frequency, the slope of this phase line characteristic can be defined as a slope gexp=tan(φexp).

The phase difference characteristic calculation unit 40a outputs the calculated comparison results (phase difference characteristics) to the determination unit 50. In other words, the comparison unit 40 (the phase difference characteristic calculation unit 40a) calculates a transfer function (at least phase difference characteristics) for the pressures between the measurement location to which the pressure cuff 24a is attached and the measurement location to which the pressure cuff 24b is attached.

The determination unit 50 determines the presence/absence of an arterial aneurysm based on a predetermined characteristic amount for the frequencies contained in the comparison results calculated by the comparison unit 40. More specifically, the determination unit 50 determines the presence/absence of an arterial aneurysm based on the degree of variation in the phase found in the phase difference characteristics regarding the calculated transfer functions.

Figure 14A:
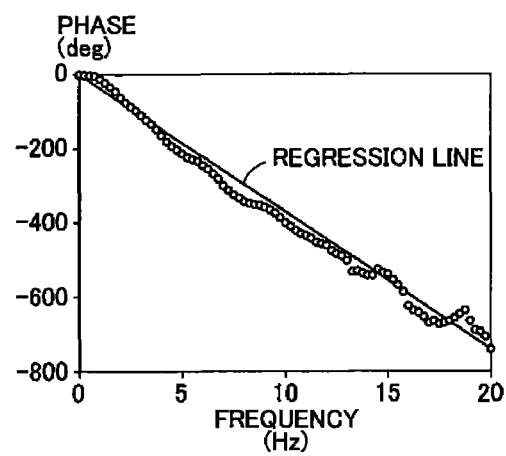
FIG. 14 is a phase diagram calculated based on actual measurement signals obtained from a plurality of measurement subjects.
Figure 14B:
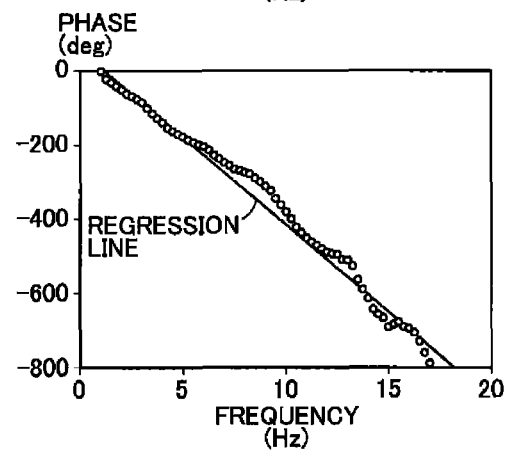
Figure 14C:
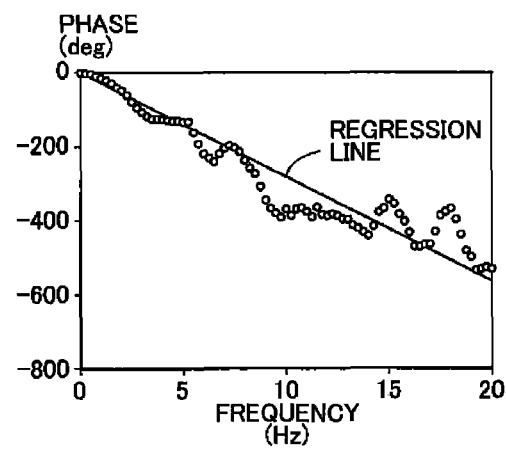

FIG. 14 is a phase diagram calculated based on actual measurement signals obtained from a plurality of measurement subjects. In other words, phase difference characteristics such as those shown in FIGS. 14(A) to (C) are outputted from the comparison unit 40. The determination unit 50 evaluates the degree of variation in the phase for the respective phase difference characteristics shown in FIGS. 14(A) to (C). As one example, the determination unit 50 sets respective regression lines determined through known methods and calculates shift amounts from the set regression lines as the degrees of variation. The determination unit 50 then determines whether or not the calculated degree of variation exceeds a predetermined threshold value. In the case where the calculated degree of variation exceeds a predetermined threshold value, it is determined that an arterial aneurysm that cannot be ignored is present in the vascular pathway being examined.

The regression lines illustrated in FIGS. 14(A) to (C) may be calculated by performing statistical processing on the phases of each measured frequency. The determination unit 50 includes a statistical processing unit 50a, and the statistical processing unit 50a determines a regression line for evaluating the degree of variation in the phase, and calculates the degree of variation the phase based on the determined regression line. Alternatively, a regression line may be determined for the phase difference characteristics using a method such as the least-squares method. Further still, the pulse wave propagation velocity may be measured in a healthy area where it is thought that no arterial aneurysm is present (for example, between the heart and the carotid artery), original phase difference characteristics may be calculated based on the measured pulse wave propagation velocity, and the regression line may be determined based on the calculated original phase difference characteristics.

For the degree of variation as well, shift amounts from the regression line may be calculated for each frequency through integration, and a total surface area between the regression line and the phase difference characteristics may be calculated. Furthermore, the degree of variation may be calculated through a known method such as standard deviation.

Referring once again to FIG. 13, the output unit 60 displays the result of the determination performed by the determination unit 50 in the display unit 4 (see FIG. 12).

d3. Processing Procedure

Next, a process for determining an arterial aneurysm according to the first embodiment will be described.

Figure 15:
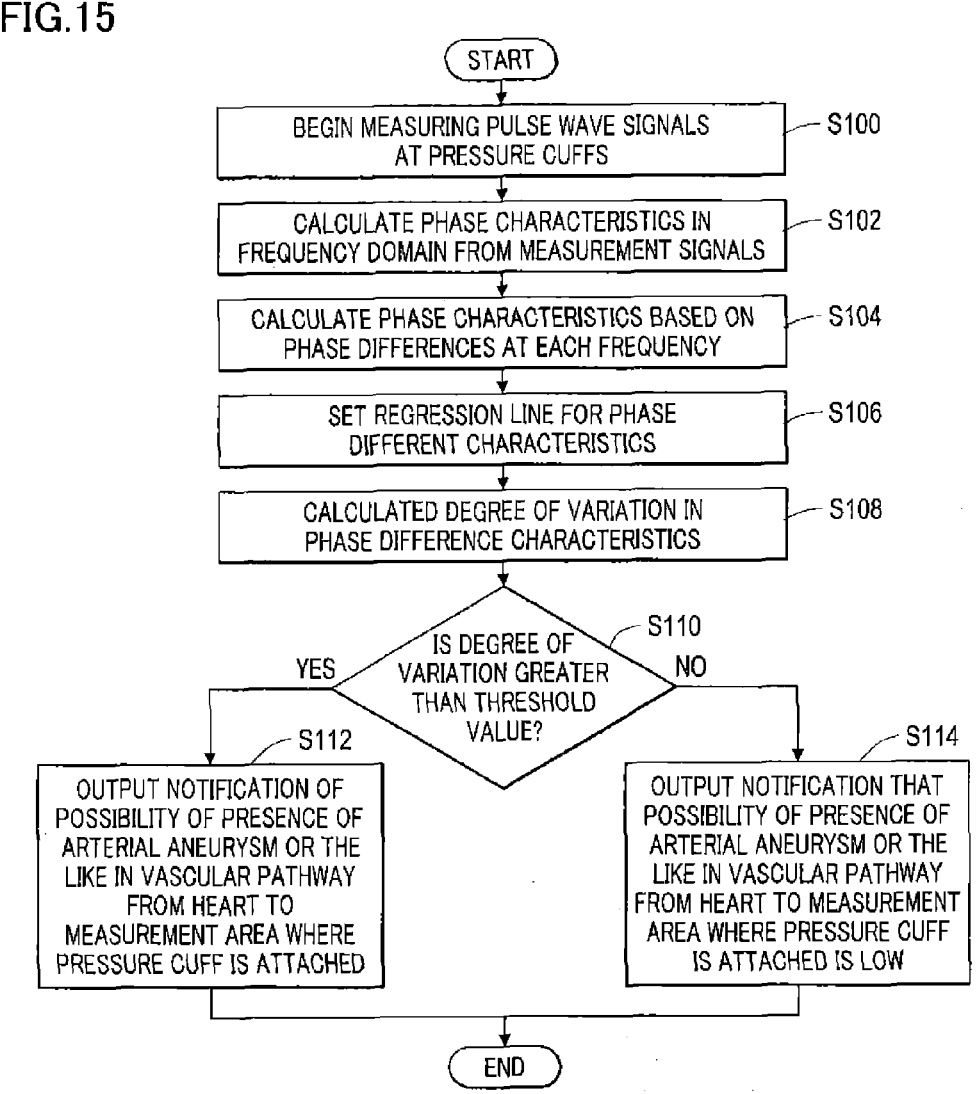
FIG. 15 is a flowchart illustrating a process for determining an arterial aneurysm according to the first embodiment.

FIG. 15 is a flowchart illustrating a process for determining an arterial aneurysm according to the first embodiment. As shown in FIG. 15, in response to a user making an operation through the operating unit 6 (see FIG. 12) or the like, the CPU 10 supplies the measurement instructions to the measurement units 20a and 20b, and the measurement units 20a and 20b begin measuring the pulse wave signals through the pressure cuffs 24a and 24b that are attached to the measurement subject 200 (step S100).

Next, the CPU 10 calculates the phase characteristics Φa(f) and Φb(f) in the frequency domain from the measurement signals Pa(t) and Pb(t), which are time waveforms measured by the measurement units 20a and 20b (step S102). Then, the CPU 10 calculates the phase difference characteristics based on the phase differences between the phase characteristics Φa(f) and the phase characteristics Φb(f) at each frequency (step S104).

Next, the CPU 10 sets a regression line for the calculated phase difference characteristics (step S106), and calculates the degree of variation in the phase difference characteristics based on the set regression line (step S108).

Thereafter, the CPU 10 compares the calculated degree of variation in the phase difference characteristics with a predetermined threshold value, and determines whether or not the degree of variation is greater than the threshold value (step S110).

In the case where the degree of variation is greater than the threshold value (YES in step S110), the CPU 10 determines that a predetermined pathologic change such as an arterial aneurysm may be present in the vascular pathway from the heart of the measurement subject 200 to the measurement locations where the pressure cuffs 24a and 24b are attached, and outputs that evaluation result to the display unit 4 (step S112). After this, the measurement process ends. On the other hand, in the case where the degree of variation is less than the threshold value (NO in step S110), the CPU 10 determines that a predetermined pathologic change such as an arterial aneurysm is unlikely to be present in the vascular pathway from the heart of the measurement subject 200 to the measurement locations where the pressure cuffs 24a and 24b are attached, and outputs that evaluation result to the display unit 4 (step S114). After this, the measurement process ends.

d4. Advantages

According to the present embodiment, the presence/absence of a pathologic change such as an arterial aneurysm can be determined simply by measuring pulse wave signals from the lower extremities and the upper extremities of a measurement subject. Accordingly, arterial aneurysm diagnoses can be made using a simpler configuration and a simpler procedure. Furthermore, according to the present embodiment, the presence/absence of a pathologic change such as an arterial aneurysm is determined using phase signals of the pulse wave signals, which can be detected with a comparatively high level of precision, which in turn makes it possible to improve the determination accuracy E. Arterial Aneurysm Determination Logic Second Embodiment e1. Overview As in the first embodiment, the second embodiment will describe a configuration in which a transfer function is calculated for pressures between a measurement location where the pressure cuff 24a is attached (a measurement location in the vascular pathway from the measurement subject's heart to an area where an arterial aneurysm is predicted to occur) and a measurement location where the pressure cuff 24b is attached (a measurement location in the vascular pathway from the measurement subject's heart to an area that is different from the area where an arterial aneurysm is predicted to occur) from the respective detected pulse wave signals, and the presence/absence and/or size of an arterial aneurysm is detected using the calculated transfer function. In the second embodiment, reference phase difference characteristics are calculated based on phase delay times for each frequency in the pulse wave signal. To be more specific, a phase angle in the phase diagram is calculated based on an average of the phase delay times for each frequency in the pulse wave signal. Then, the presence/absence and size of an arterial aneurysm is detected based on the number of times the reference phase difference characteristics and the phase difference characteristics regarding the transfer function intersect, or based on the frequency interval of the intersection. As described above, in the phase diagram for the transfer function, the phase changes by 180 degrees with each fundamental frequency. This phase appears with greater frequency in the case where the fundamental frequency is low (narrow). Furthermore, because the fundamental frequency is in an inverse proportion with the length of the arterial aneurysm, there is a higher likelihood that an arterial aneurysm is present in cases where the fundamental frequency is relatively low (narrow). Accordingly, by using a phase delay that can arise based on the state of the vascular pathways of the measurement subject as a reference, the presence and size (inner diameter and length) of an arterial aneurysm can be estimated based on a shift from these reference characteristics.

The second embodiment differs from the first embodiment primarily in terms of a process for calculating the reference phase difference characteristics and a process for evaluating a shift from the reference characteristics. Accordingly, the following descriptions will focus primarily on these differences.

e2. Functional Configuration

Figure 16:
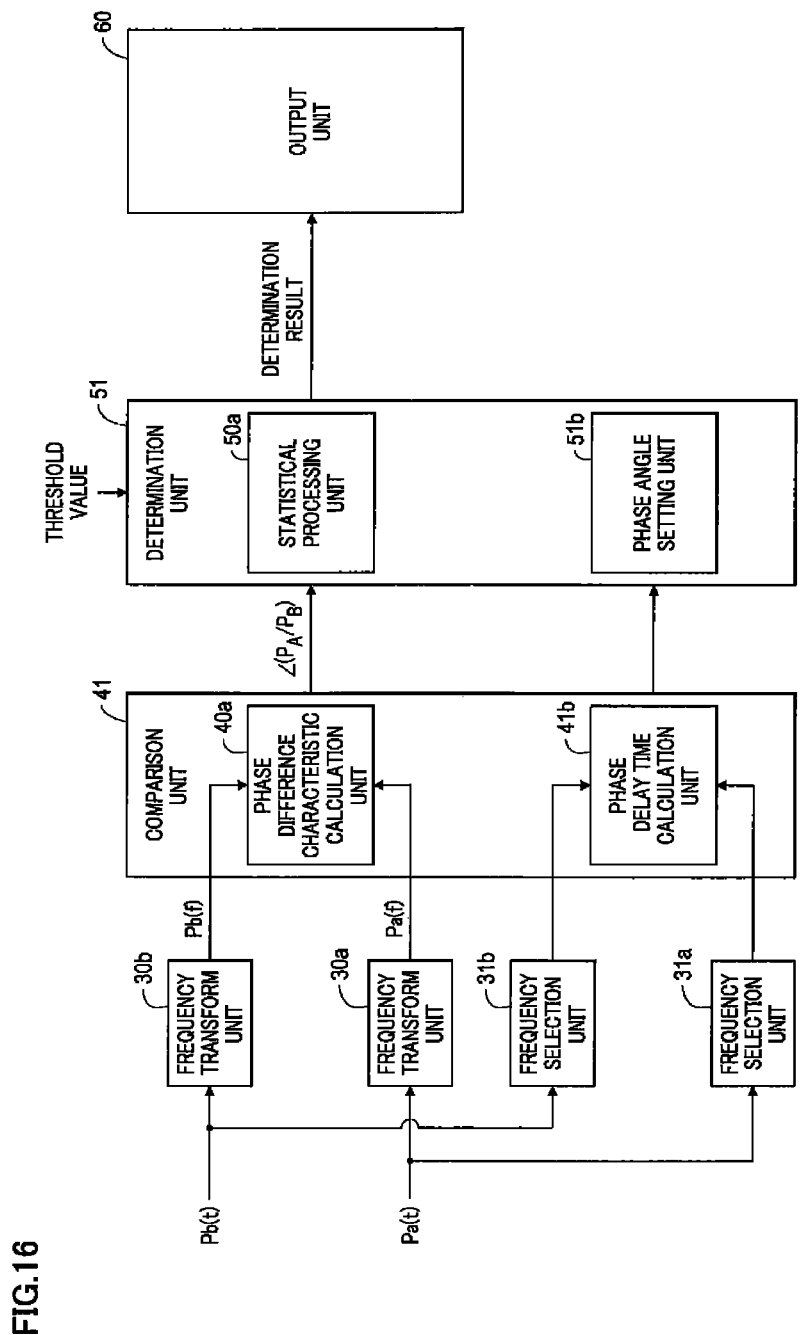
FIG. 16 is a schematic diagram illustrating functional blocks that implement processes for detecting an arterial aneurysm according to a second embodiment.

FIG. 16 is a schematic diagram illustrating functional blocks that implement processes for detecting an arterial aneurysm according to the second embodiment. Typically, the functional blocks illustrated in FIG. 16 are realized by the CPU 10 of the processing unit 2 (see FIG. 12) executing computational processes in accordance with a program stored in advance in the ROM 12 or the like.

As shown in FIG. 16, the processing unit 2 according to the second embodiment includes the frequency transform units 30a and 30b, frequency selection units 31a and 31b, a comparison unit 41, a determination unit 51, and the output unit 60. The frequency transform units 30a and 30b and the output unit 60 have already been described with reference to FIG. 13, and thus detailed descriptions thereof will not be repeated.

To calculate the phase delay times for each frequency in the pulse wave signals, the frequency selection units 31a and 31b extract only specific frequency components contained in the measurement signals Pa(t) and Pb(t), respectively, and output those components to the comparison unit 41. The frequency selection units 31a and 31b function as what are known as band pass filters. Here, because it is necessary for the frequency selection units 31a and 31b to extract the same frequency components, the units are linked so that the extracted frequencies are synchronized.

The comparison unit 41 includes a phase delay time calculation unit 41a in addition to the phase difference characteristic calculation unit 40a described in the first embodiment. The phase delay time calculation unit 41a calculates the phase delay times for each frequency in the pulse wave signals by comparing the extracted specific frequency components contained in the measurement signals Pa(t) and Pb(t) obtained from the frequency selection units 31a and 31b, respectively.

The determination unit 51 includes a phase angle setting unit 51a in addition to the statistical processing unit 50a described in the first embodiment. The phase angle setting unit 51a calculates a phase angle based on an average of the phase delay times for each frequency calculated by the phase delay time calculation unit 41a. This phase angle indicates a phase delay that can arise based on the state of the vascular pathways of the measurement subject.

Figure 17A:
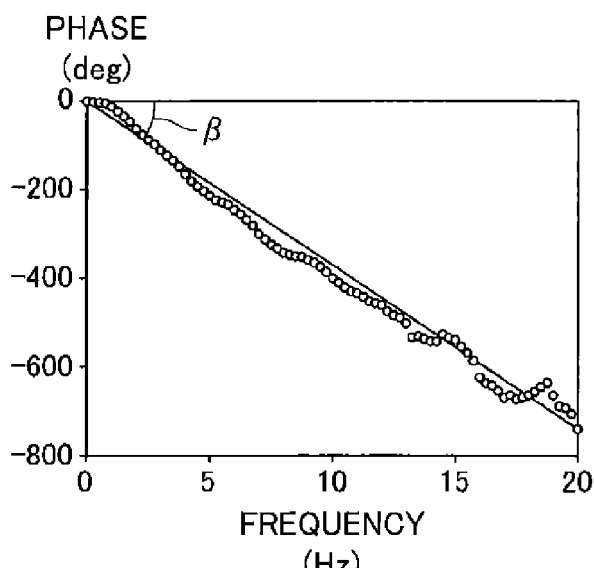
FIG. 17 is a diagram illustrating a phase angle (reference phase difference characteristics) set by a phase angle setting unit according to the second embodiment.
Figure 17B:
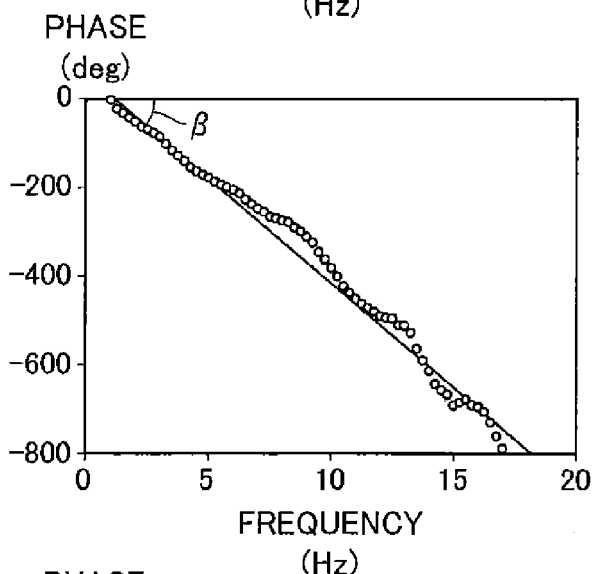
Figure 17C:
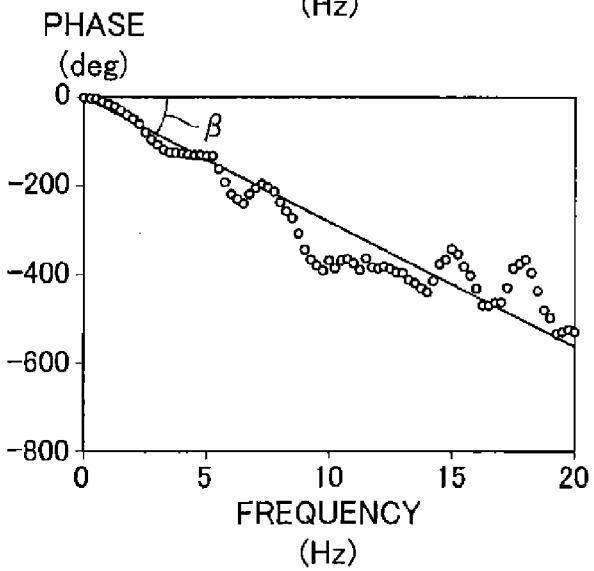

FIG. 17 is a diagram illustrating a phase angle (reference phase difference characteristics) set by the phase angle setting unit 51a according to the second embodiment. As shown in FIGS. 17(A) to (C), the reference phase difference characteristics are set based on a phase angle β calculated by the phase angle setting unit 51a. This phase angle β indicates a slope in a phase diagram.

The determination unit 51 evaluates the presence/absence and/or size of an arterial aneurysm based on a state in which the phase difference characteristics in the pulse wave signals calculated by the phase difference characteristic calculation unit 40a intersect with the reference phase difference characteristics set by the phase angle setting unit 51a.

As described above, in the phase diagram for the transfer function, the phase changes by 180 degrees with each fundamental frequency. This phase appears with greater frequency in the case where the fundamental frequency is low (narrow). Furthermore, because the fundamental frequency is in an inverse proportion with the length of the arterial aneurysm, there is a higher likelihood that an arterial aneurysm is present in cases where the fundamental frequency is relatively low (narrow). Accordingly, the presence of an arterial aneurysm can be determined with a higher level of certainty the greater the number of intersections between the phase difference characteristics in the pulse wave signals and the reference phase difference characteristics is. Furthermore, because the fundamental frequency is in an inverse proportion with the length of the arterial aneurysm, it can be estimated that a longer arterial aneurysm is present in cases where the fundamental frequency is relatively low (narrow).

Meanwhile, because the frequency interval where the reference phase difference characteristics and the phase difference characteristics in the pulse wave signals intersect is the aforementioned fundamental frequency itself, the presence/absence and/or size of an arterial aneurysm can also be estimated based on the frequency interval of intersection.

In other words, in the second embodiment, the determination unit 51 determines the presence/absence and/or size of an arterial aneurysm based on the number of times the phase difference characteristics of the transfer functions intersect with the phase angle calculated based on the average of the phase delay times at each frequency. Alternatively, the determination unit 51 determines the presence/absence and/or size of an arterial aneurysm based on the frequency interval where the phase difference characteristics of the transfer functions intersect with the phase angle calculated based on the average of the phase delay times at each frequency.

Note that there may be error in the phase difference characteristics calculated from the measurement signals Pa(t) and Pb(t), and thus the influence of such error may be reduced by using specific frequency components, interpolating the phase difference characteristics, and so on.

e3. Processing Procedure

Next, a process for determining an arterial aneurysm according to the second embodiment will be described.

Figure 18:
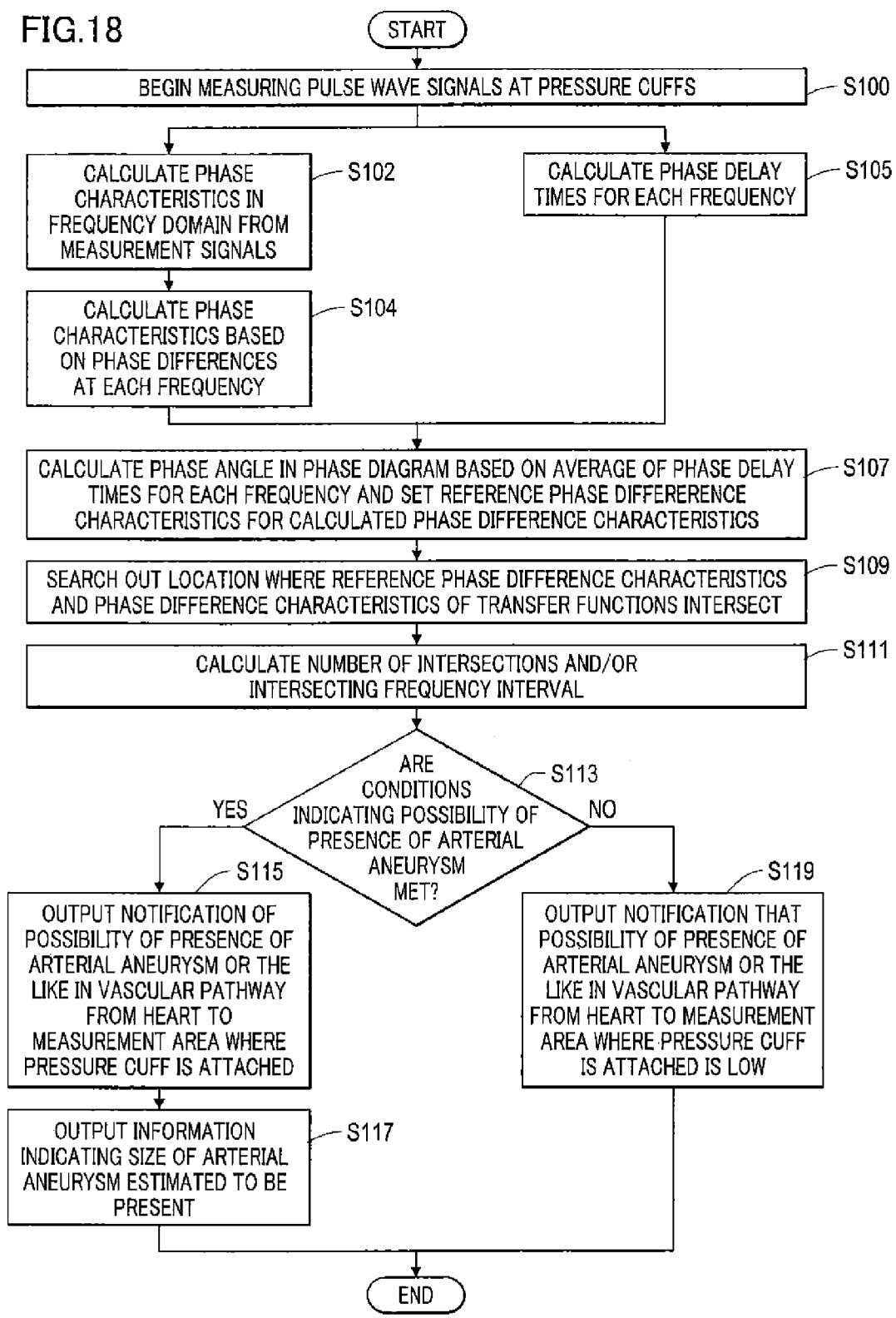
FIG. 18 is a flowchart illustrating a process for determining an arterial aneurysm according to the second embodiment.

FIG. 18 is a flowchart illustrating a process for determining an arterial aneurysm according to the second embodiment. Note that in the flowchart illustrated in FIG. 18, processes that are the same as those in the flowchart illustrated in FIG. 15 have been given the same step numbers.

As shown in FIG. 18, in response to a user making an operation through the operating unit 6 (see FIG. 12) or the like, the CPU 10 supplies the measurement instructions to the measurement units 20a and 20b, and the measurement units 20a and 20b begin measuring the pulse wave signals through the pressure cuffs 24a and 24b that are attached to the measurement subject 200 (step S100).

Next, the CPU 10 calculates the phase characteristics Φa(f) and Φb(f) in the frequency domain from the measurement signals Pa(t) and Pb(t), which are time waveforms measured by the measurement units 20a and 20b (step S102). Then, the CPU 10 calculates the phase difference characteristics based on the phase differences between the phase characteristics Φa(f) and the phase characteristics Φb(f) at each frequency (step S104). In parallel with or following the processes of steps S102 and S104, the CPU 10 calculates the phase delay times for each frequency in the measurement signals Pa(t) and Pb(t) (step S105).

Next, the CPU 10 calculates the phase angle in the phase diagram based on an average of the phase delay times for each frequency as calculated in step S105, and sets the reference phase difference characteristics for the calculated phase difference characteristics (step S107). The CPU 10 then searches out a location where the reference phase difference characteristics and the phase difference characteristics regarding the transfer functions intersect (step S109), and calculates the number of intersecting locations (number of intersections) and/or an interval between intersecting locations (intersecting frequency interval) (step S111).

Next, the CPU 10 determines whether or not conditions that indicate an arterial aneurysm may be present are met based on the information calculated in step S111 (step S113). More specifically, the CPU 10 determines whether or not the number of intersections calculated in step S111 exceeds a predetermined threshold number, or whether or not the intersecting frequency interval calculated in step S111 is less than a predetermined threshold frequency.

In the case where the conditions that indicate an arterial aneurysm may be present are met (YES in step S113), the CPU 10 determines that a predetermined pathologic change such as an arterial aneurysm may be present in the vascular pathway from the heart of the measurement subject 200 to the measurement locations where the pressure cuffs 24a and 24b are attached, and outputs that evaluation result to the display unit 4 (step S115). Furthermore, the CPU 10 outputs information indicating the size of the arterial aneurysm estimated to be present to the display unit 4 based on the value of the intersecting frequency interval calculated in step S111 (step S117). After this, the measurement process ends.

On the other hand, in the case where the conditions that indicate an arterial aneurysm may be present are not met (NO in step S110), the CPU 10 determines that a predetermined pathologic change such as an arterial aneurysm is unlikely to be present in the vascular pathway from the heart of the measurement subject 200 to the measurement locations where the pressure cuffs 24a and 24b are attached, and outputs that evaluation result to the display unit 4 (step S119). After this, the measurement process ends.

e4. Advantages

According to the present embodiment, the presence/absence of a pathologic change such as an arterial aneurysm can be determined simply by measuring pulse wave signals from the lower extremities and the upper extremities of a measurement subject. Accordingly, arterial aneurysm diagnoses can be made using a simpler configuration and a simpler procedure. Furthermore, according to the present embodiment, the size of an arterial aneurysm can be estimated in addition to the presence/absence thereof, and thus the degree to which the arterial aneurysm whose presence has been estimated has advanced can also be estimated.

F. Arterial Aneurysm Determination Logic

Third Embodiment f1. Overview

As in the first and second embodiments, the third embodiment will describe a configuration in which a transfer function is calculated for pressures between a measurement location where the pressure cuff 24a is attached (a measurement location in the vascular pathway from the measurement subject's heart to an area where an arterial aneurysm is predicted to occur) and a measurement location where the pressure cuff 24b is attached (a measurement location in the vascular pathway from the measurement subject's heart to an area that is different from the area where an arterial aneurysm is predicted to occur) from the respective detected pulse wave signals, and the presence/absence and/or size of an arterial aneurysm is detected using the calculated transfer function. In the third embodiment, the presence/absence and/or size of an arterial aneurysm is detected based on a frequency interval at which extreme values appear in gain characteristics of the transfer function. As described above, in the gain diagram for the transfer function, the frequency interval where extreme values (maximum value/minimum value) appear is the fundamental frequency and the fundamental frequency is in an inverse proportion with the length of the arterial aneurysm; accordingly, there is a higher likelihood that an arterial aneurysm is present in cases where the fundamental frequency is relatively low (narrow).

Accordingly, in the third embodiment, gain characteristics ($|P_A/P_B|$) of the transfer function $P_A/P_B$ are calculated by calculating the gain characteristics of the measurement signals Pa(t) and Pb(t) by performing frequency transforms thereon, and furthermore calculating gain ratios at each frequency. Note that for the sake of simplicity, descriptions will be given using gain characteristics Ga(f) and Gb(f), which can be defined through the following Formula (41) using the respective Fourier signals Pa(f) and Pb(f).

$$G_a(f) = |P_a(f)|$$

$$G_b(f) = |P_b(f)| \qquad (41)$$

Note that in the case where a log value (decibels (dB)) is used as the gain characteristics Ga(f) and Gb(f), the differences between the gain characteristics Ga(f) and the gain characteristics Gb(f) at each frequency serve as the gain characteristics.

It is then determined whether or not an arterial aneurysm is present in the vascular pathway in question based on the frequency interval at which the extreme values (maximum value/minimum value) appear in the calculated gain characteristics of the transfer functions. The size (length) of the arterial aneurysm is estimated as well. An example of a specific configuration for realizing such processing will be described hereinafter.

f2. Functional Configuration

Figure 19:
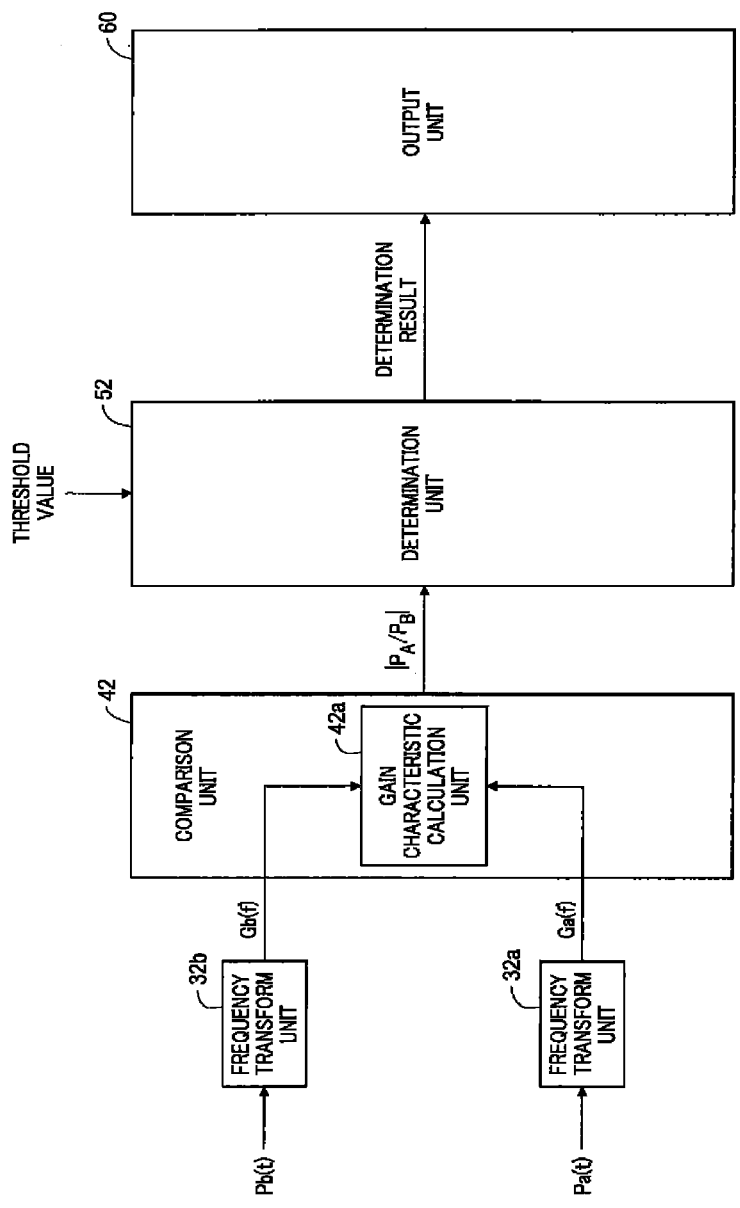
FIG. 19 is a schematic diagram illustrating functional blocks that implement processes for detecting an arterial aneurysm according to a third embodiment.

FIG. 19 is a schematic diagram illustrating functional blocks that implement processes for detecting an arterial aneurysm according to the third embodiment. Typically, the functional blocks illustrated in FIG. 19 are realized by the CPU 10 of the processing unit 2 (see FIG. 12) executing computational processes in accordance with a program stored in advance in the ROM 12 or the like.

As shown in FIG. 19, the processing unit 2 according to the third embodiment includes frequency transform units 32a and 32b, a comparison unit 42, a determination unit 52, and the output unit 60.

The frequency transform units 32a and 32b receive the measurement signals Pa(t) and Pb(t), which are time waveforms, over a predetermined period, and transform the received measurement signals Pa(t) and Pb(t) into frequency domain information. Generally, the frequency transform units 32a and 32b carry out the frequency transforms using fast Fourier transforms (FFT). Note that the embodiment is not limited to fast Fourier transforms, and any transform algorithm may be used as long as it transforms a time-domain signal into a frequency-domain signal such as a Fourier series.

In the third embodiment, the frequency transform units 32a and 32b output the gain characteristics Ga(f) and Gb(f) as the frequency-domain information. More specifically, the frequency transform unit 32a calculates the gain characteristics Ga(f) indicating a gain for each frequency component in the measurement signal Pa(t), and outputs the calculated phase characteristic Ga(f) to the comparison unit 42. Likewise, the frequency transform unit 32b calculates the gain characteristics Gb(f) indicating a gain for each frequency component in the measurement signal Pb(t), and outputs the calculated gain characteristics Gb(f) to the comparison unit 42.

The comparison unit 42 calculates the gain ratio in each frequency as comparison results, by comparing the frequency characteristics (in the third embodiment, gain characteristics) between the measurement signals Pa(t) and Pb(t), which are pulse wave signals. To be more specific, the comparison unit 42 includes a gain characteristic calculation unit 42a. The gain characteristic calculation unit 42a calculates gain characteristics indicating the gain ratio for each frequency by calculating the ratio (or difference) between the gain characteristics Ga(f) and the gain characteristics Gb(t) for each frequency. The comparison results (gain characteristics) calculated by the comparison unit 42 are outputted to the determination unit 52. In other words, the comparison unit 42 calculates a transfer function (at least gain characteristics) for the pressures between the measurement location to which the pressure cuff 24a is attached and the measurement location to which the pressure cuff 24b is attached.

The determination unit 52 determines the presence/absence of an arterial aneurysm based on a predetermined characteristic amount for the frequencies contained in the comparison results calculated by the comparison unit 42. More specifically, the determination unit 52 determines the presence/absence and/or size of an arterial aneurysm based on the frequency interval at which extreme values (maximum value/minimum value) appear in the calculated gain characteristics of the transfer functions.

Figure 20:
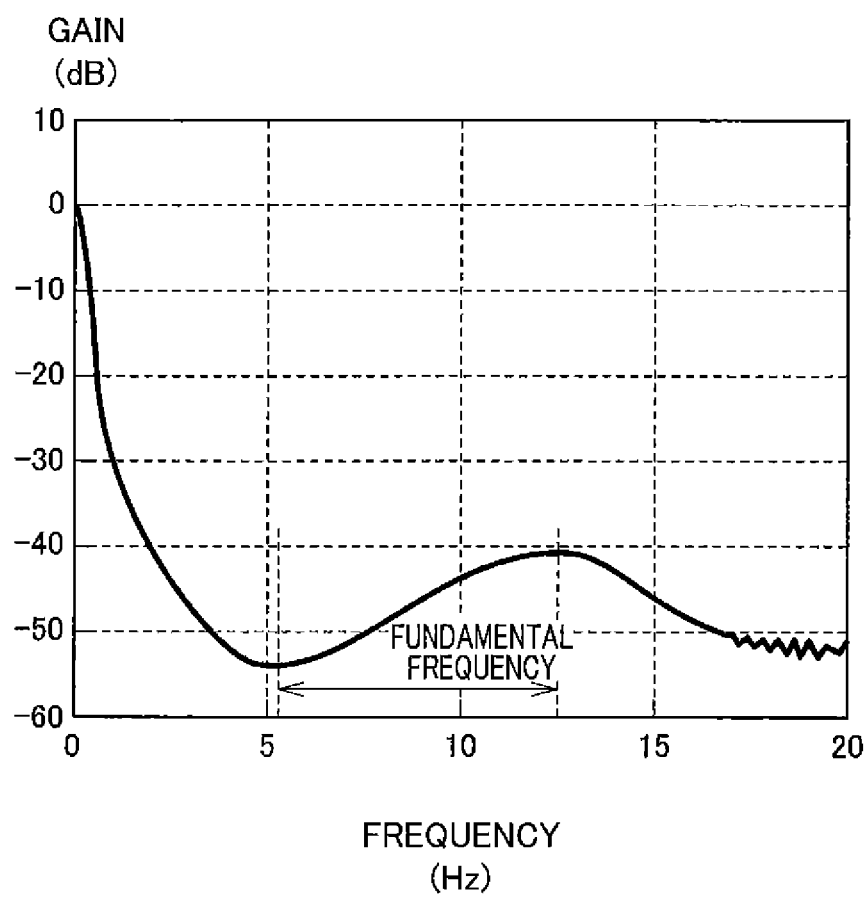
FIG. 20 is a diagram illustrating a determination process performed by a determination unit according to the third embodiment.

FIG. 20 is a diagram illustrating a determination process performed by the determination unit 52 according to the third embodiment. Gain characteristics such as those shown in FIG. 20 are outputted from the comparison unit 42. The determination unit 52 searches out the extreme values (a maximum value and a minimum value) in the gain characteristics illustrated in FIG. 20. A known method may be employed as the method for searching for the extreme values. Then, the determination unit 52 calculates the frequency interval between adjacent extreme values searched out in this manner as the fundamental frequency. Although there may be cases where the frequency interval varies depending on the position where the extreme values are present due to some sort of measurement error or the like, it should be noted that an average of a plurality of frequency intervals may be set as the fundamental frequency in such a case.

Then, based on the magnitude of the calculated fundamental frequency, the determination unit 52 determines whether or not an arterial aneurysm that cannot be ignored is present in the vascular pathway being examined, and in the case where the presence of an arterial aneurysm has been determined to be highly likely, the size thereof is estimated from the fundamental frequency. Typically, the determination unit 52 compares the calculated fundamental frequency to a predetermined threshold value, and determines that the presence of an arterial aneurysm is highly likely in the case where the fundamental frequency is lower than the threshold value.

f3. Processing Procedure

Next, a process for determining an arterial aneurysm according to the third embodiment will be described.

Figure 21:
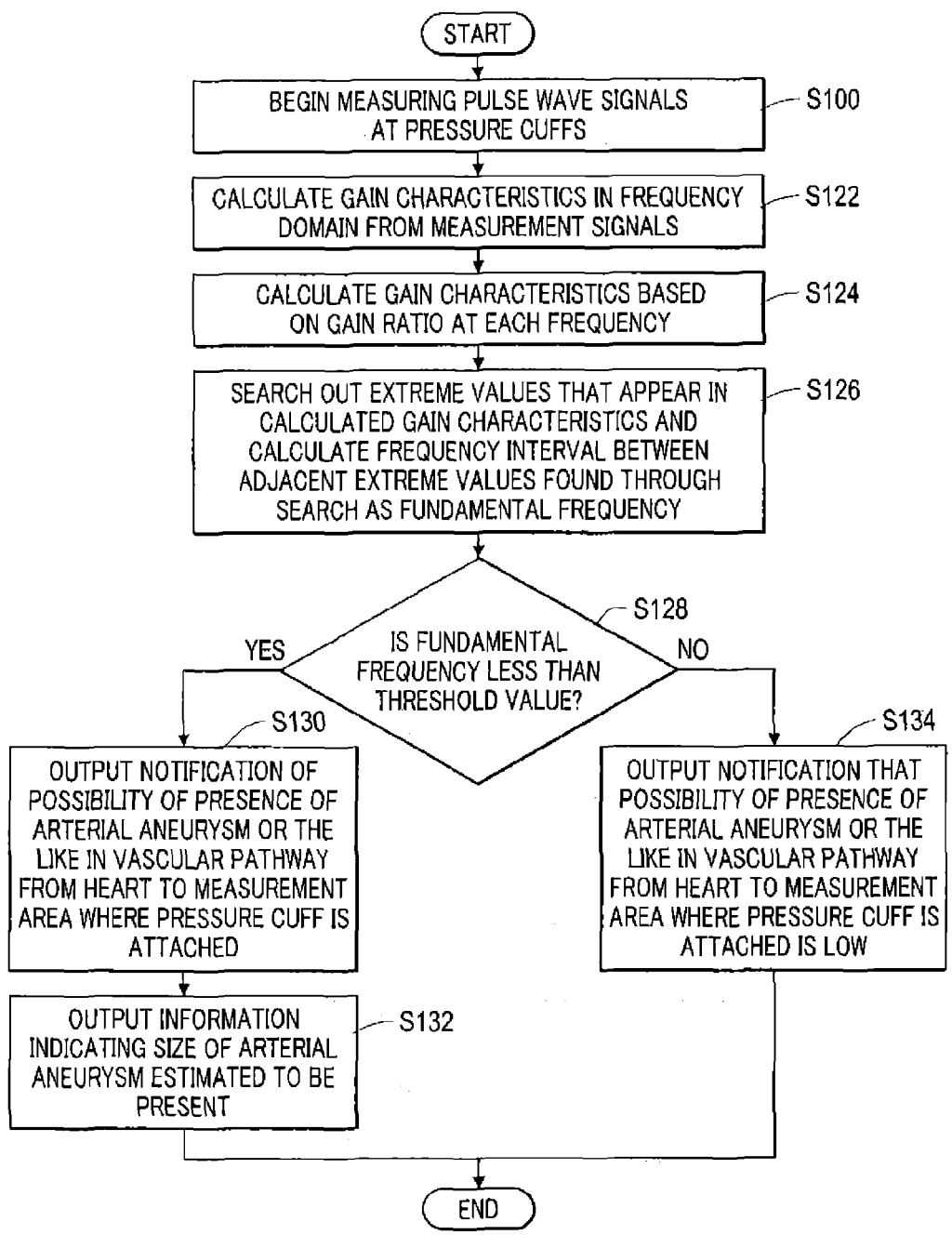
FIG. 21 is a flowchart illustrating a process for determining an arterial aneurysm according to the third embodiment.

FIG. 21 is a flowchart illustrating a process for determining an arterial aneurysm according to the third embodiment. Note that in the flowchart illustrated in FIG. 21, processes that are the same as those in the flowchart illustrated in FIG. 15 have been given the same step numbers.

As shown in FIG. 21, in response to a user making an operation through the operating unit 6 (see FIG. 12) or the like, the CPU 10 supplies the measurement instructions to the measurement units 20a and 20b, and the measurement units 20a and 20b begin measuring the pulse wave signals through the pressure cuffs 24a and 24b that are attached to the measurement subject 200 (step S100).

Next, the CPU 10 calculates the gain characteristics Ga(f) and Gb(f) in the frequency domain from the measurement signals Pa(t) and Pb(t), which are time waveforms measured by the measurement units 20a and 20b (step S122). Then, the CPU 10 calculates the gain characteristics based on the gain ratio between the gain characteristics Ga(f) and the gain characteristics Gb(f) at each frequency (step S124).

Next, the CPU 10 searches out the extreme values (maximum value and minimum value) that appear in the calculated gain characteristics, and calculates the frequency interval between adjacent extreme values found through the search as the fundamental frequency (step S126).

Thereafter, the CPU 10 compares the calculated fundamental frequency with a predetermined threshold value and determines whether or not the fundamental frequency is lower than the threshold value (step S128).

In the case where the fundamental frequency is less than the threshold value (YES in step S128), the CPU 10 determines that a predetermined pathologic change such as an arterial aneurysm may be present in the vascular pathway from the heart of the measurement subject 200 to the measurement locations where the pressure cuffs 24a and 24b are attached, and outputs that evaluation result to the display unit 4 (step S130). Furthermore, the CPU 10 outputs information indicating the size of the arterial aneurysm estimated to be present to the display unit 4 based on the magnitude of the fundamental frequency (step S132). After this, the measurement process ends. On the other hand, in the case where the fundamental frequency is greater than the threshold value (NO in step S128), the CPU 10 determines that a predetermined pathologic change such as an arterial aneurysm is unlikely to be present in the vascular pathway from the heart of the measurement subject 200 to the measurement locations where the pressure cuffs 24a and 24b are attached, and outputs that evaluation result to the display unit 4 (step S134). After this, the measurement process ends.

f4. Advantages

According to the present embodiment, the presence/absence of a pathologic change such as an arterial aneurysm can be determined simply by measuring pulse wave signals from the lower extremities and the upper extremities of a measurement subject. Accordingly, arterial aneurysm diagnoses can be made using a simpler configuration and a simpler procedure. Furthermore, according to the present embodiment, the fundamental frequency can be calculated directly, and thus the size of an arterial aneurysm can be estimated with a higher level of accuracy.

G. Arterial Aneurysm Determination Logic

Fourth Embodiment g1. Overview

In the fourth embodiment, the frequency characteristics are calculated with respect to the pulse wave propagation velocities in the detected pulse wave signals, and the presence/absence and/or size of an arterial aneurysm is detected based on variation between the pulse wave propagation velocities and/or a frequency interval of fluctuations in the pulse wave propagation velocities found in the frequency characteristics for the calculated pulse wave propagation velocities.

The pulse wave propagation velocity indicates a characteristic amount corresponding to the phase difference characteristics used in the first embodiment, and indicates a characteristic amount corresponding to the phase delay time in the second embodiment. For this reason, the pulse wave propagation velocity indicates a characteristic amount for the same frequency as the phase difference characteristics, the phase delay time, and so on.

Accordingly, in the fourth embodiment, the presence/absence and/or size of an arterial aneurysm is detected from the frequency characteristics with respect to the pulse wave propagation velocity, using the same determination method as that used in the aforementioned first or second embodiment.

g2. Functional Configuration

Figure 22:
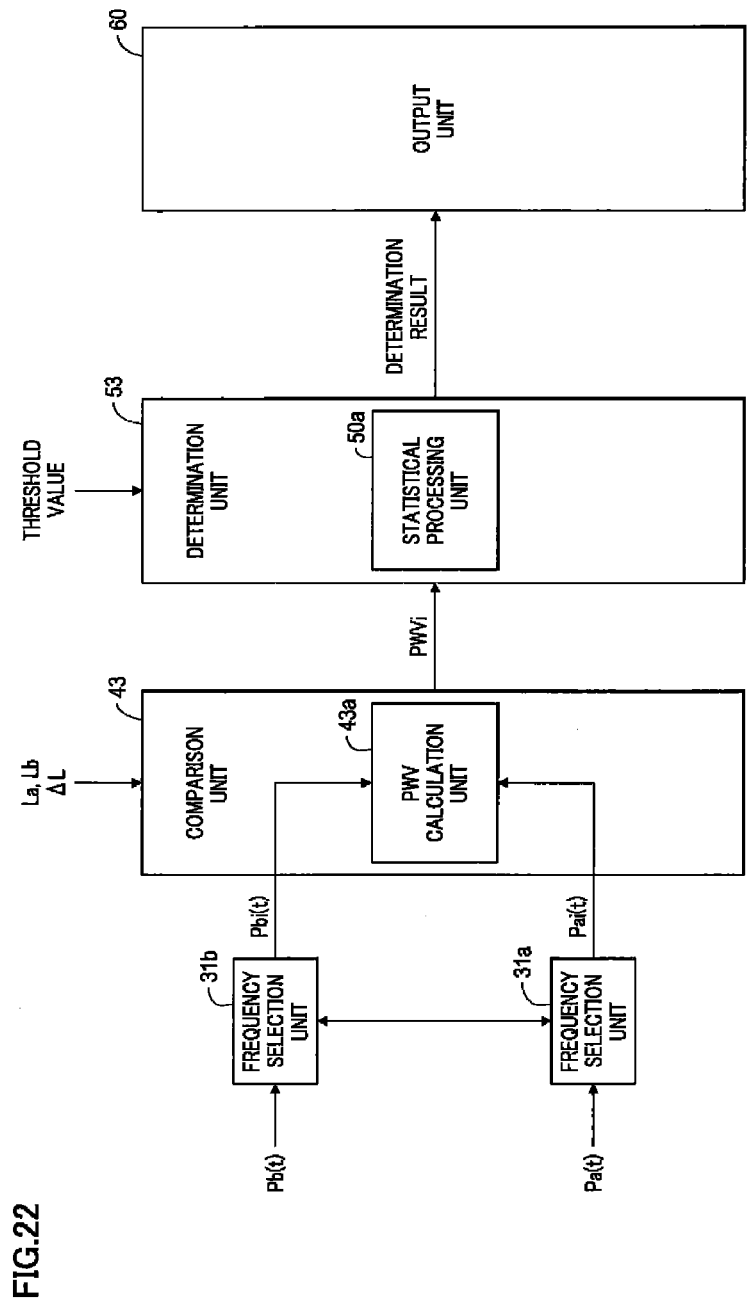
FIG. 22 is a schematic diagram illustrating functional blocks that implement processes for detecting an arterial aneurysm according to a fourth embodiment.

FIG. 22 is a schematic diagram illustrating functional blocks that implement processes for detecting an arterial aneurysm according to the fourth embodiment. Typically, the functional blocks illustrated in FIG. 22 are realized by the CPU 10 of the processing unit 2 (see FIG. 12) executing computational processes in accordance with a program stored in advance in the ROM 12 or the like.

As shown in FIG. 22, the processing unit 2 according to the fourth embodiment includes the frequency selection units 31a and 31b, a comparison unit 43, a determination unit 53, and the output unit 60.

To calculate the pulse wave propagation velocity (PWV) for each frequency in the pulse wave signals, the frequency selection units 31a and 31b extract only specific frequency components contained in the measurement signals Pa(t) and Pb(t), respectively, and output those components to the comparison unit 43. The frequency selection units 31a and 31b function as what are known as band pass filters. Here, because it is necessary for the frequency selection units 31a and 31b to extract the same frequency components, the units are linked so that the extracted frequencies are synchronized.

The comparison unit 43 calculates the frequency characteristics between the measurement signals Pa(t) and Pb(t), which are pulse wave signals, with respect to the pulse wave propagation velocity, as comparison results. The comparison unit 43 includes a PWV calculation unit 43a. The PWV calculation unit 43a receives the measurement signals Pa(t) and Pb(t) over a predetermined period, and calculates a difference in times when the respective pulse waveforms appear on the time axis for each frequency as a propagation time difference $Td_i$. In other words, the frequency selection units 31a and 31b output time waveforms corresponding to the selected frequency components of the measurement signals Pa(t) and Pb(t) to the PWV calculation unit 43a, and thus the difference in times when the pulse waveforms appear serves as the propagation time difference $Td_i$ for each frequency.

Then, the PWV calculation unit 43a obtains distances La and Lb of respective vascular pathways from the heart of the measurement subject 200 to the measurement areas where the pressure cuffs 24a and 24b are attached or a distance difference ΔL, and calculates the pulse wave propagation velocity ($PWV_i$) for each frequency by dividing the distance difference ΔL by the propagation time difference $Td_i$. The PWV calculation unit 43a outputs the calculated pulse wave propagation velocity ($PWV_i$) for each frequency to the determination unit 53.

In this manner, the comparison unit 43 (the PWV calculation unit 43a) calculates the frequency characteristics with respect to the pulse wave propagation velocities between the pulse wave signals.

The determination unit 53 determines the presence/absence and/or size of an arterial aneurysm based on a predetermined characteristic amount for the frequencies contained in the frequency characteristics for the pulse wave propagation velocities between the pulse wave signals as calculated by the comparison unit 43. More specifically, the determination unit 53 determines the presence/absence and/ or size of an arterial aneurysm based on a degree of variation between the pulse wave propagation velocities and/or a frequency interval of fluctuations appearing in the pulse wave propagation velocities found in the frequency characteristics with respect to the calculated pulse wave propagation velocities.

Figure 23A:
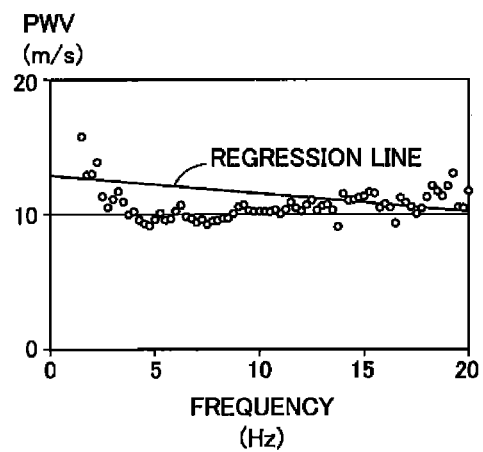
FIG. 23 is a diagram illustrating pulse wave propagation velocities calculated based on actual measurement signals obtained from a plurality of measurement subjects.
Figure 23B:
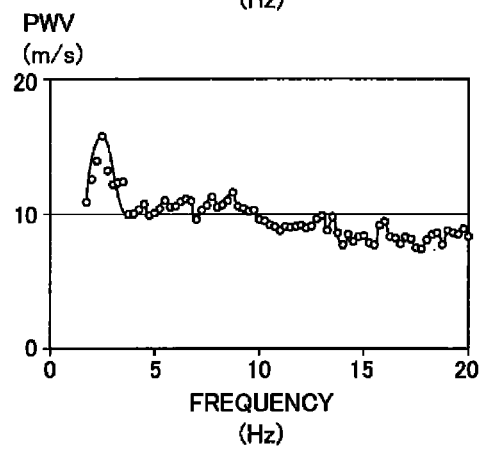
Figure 23C:
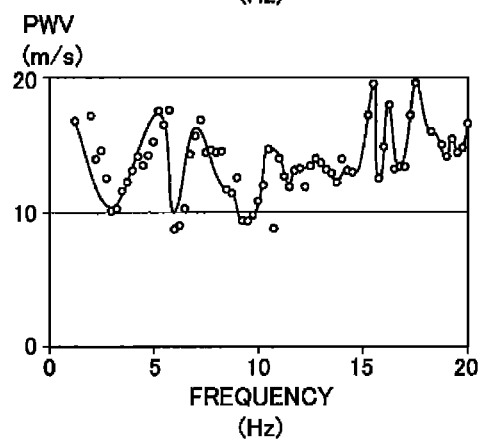

FIG. 23 is a diagram illustrating pulse wave propagation velocities (PWV) calculated based on actual measurement signals obtained from a plurality of measurement subjects. In other words, frequency characteristics with respect to pulse wave propagation velocities such as those shown in FIGS. 23(A) to (C) are outputted from the comparison unit 43. The determination unit 53 evaluates the degree of variation in the pulse wave propagation velocities and/or the frequency interval of fluctuations appearing in the pulse wave propagation velocities for the phase difference characteristics illustrated in each of FIGS. 23(A) to (C).

Typically, the determination unit 53 sets respective regression lines determined through known methods and calculates shift amounts from the set regression lines as the degrees of variation. FIG. 23(A) illustrates one example of the set regression line. The determination unit 53 then determines whether or not the calculated degree of variation exceeds a predetermined threshold value. In the case where the calculated degree of variation exceeds a predetermined threshold value, it is determined that an arterial aneurysm that cannot be ignored is present in the vascular pathway being examined.

Meanwhile, the determination unit 53 may determine the presence/absence and/or size of an arterial aneurysm based on the frequency interval of fluctuations appearing in the pulse wave propagation velocities. In FIGS. 23(B) and (C), cyclic fluctuations appear in the pulse wave propagation velocities. The determination unit 53 calculates the fluctuation cycle, or in other words, the frequency interval of the fluctuation, for such cyclic fluctuations in the pulse wave propagation velocities. The frequency interval of the fluctuation corresponds to the aforementioned fundamental frequency, and thus the presence and/or length of an arterial aneurysm can be evaluated based on the magnitude of the fundamental frequency. Based on the calculated frequency interval of the fluctuation, the determination unit 53 determines whether or not an arterial aneurysm that cannot be ignored is present in the vascular pathway being examined, and in the case where the presence of an arterial aneurysm has been determined to be highly likely, the size thereof is estimated from the frequency interval of the fluctuation.

g3. Processing Procedure

Next, a process for determining an arterial aneurysm according to the fourth embodiment will be described.

Figure 24:
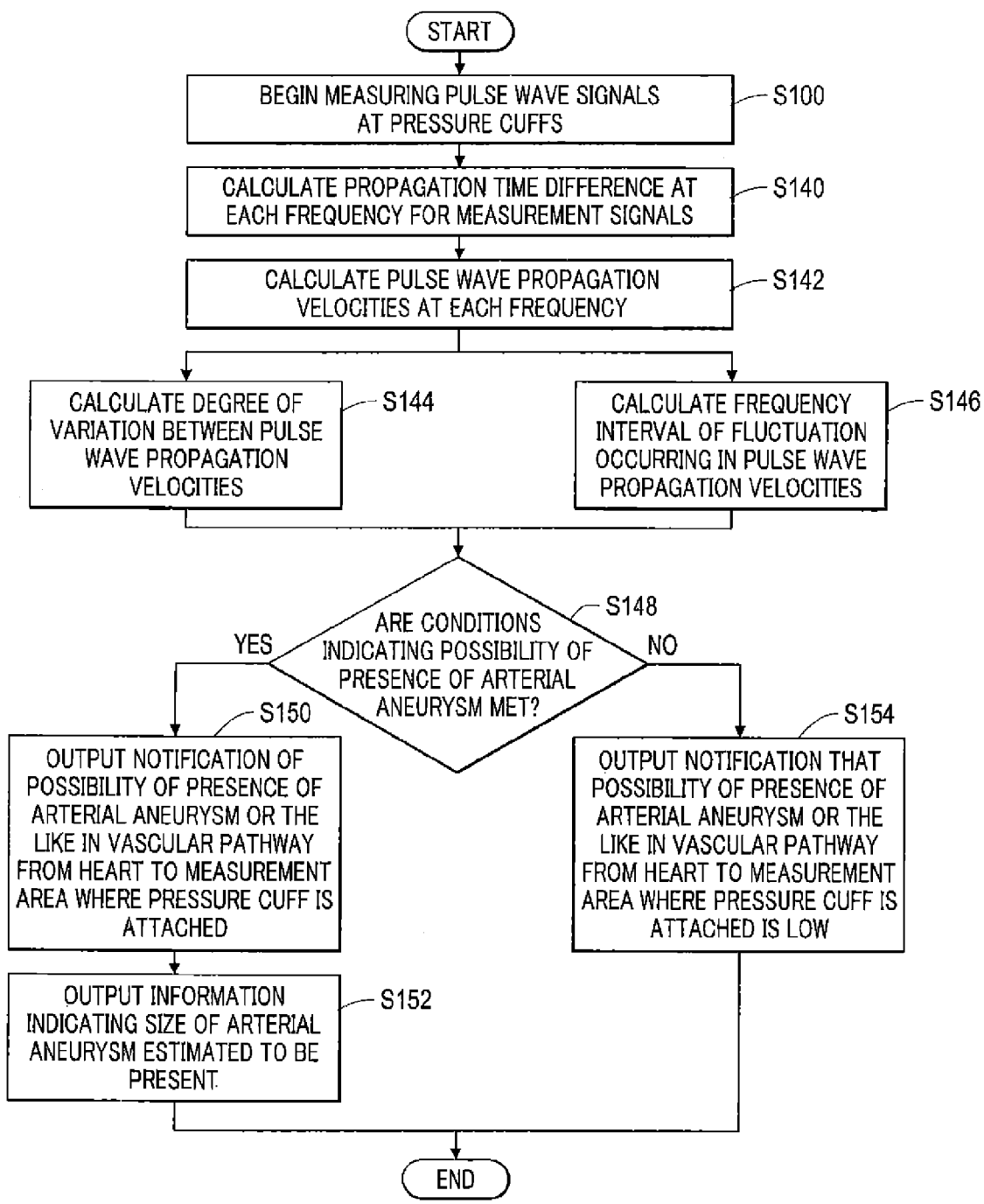
FIG. 24 is a flowchart illustrating a process for determining an arterial aneurysm according to the fourth embodiment.

FIG. 24 is a flowchart illustrating a process for determining an arterial aneurysm according to the fourth embodiment. Note that in the flowchart illustrated in FIG. 24, processes that are the same as those in the flowchart illustrated in FIG. 15 have been given the same step numbers.

As shown in FIG. 24, in response to a user making an operation through the operating unit 6 (see FIG. 12) or the like, the CPU 10 supplies the measurement instructions to the measurement units 20a and 20b, and the measurement units 20a and 20b begin measuring the pulse wave signals through the pressure cuffs 24a and 24b that are attached to the measurement subject 200 (step S100).

Next, the CPU 10 calculates the propagation time difference at each frequency for the measurement signals Pa(t) and Pb(t) (step S140), and calculates the pulse wave propagation velocities at each frequency by dividing the differences in the vascular pathways from the heart of the measurement subject to the measurement areas where the pressure cuffs 24a and 24b are attached by the propagation time difference (step S142).

Then, the CPU 10 calculates the degree of variation in the pulse wave propagation velocities for the frequency characteristics with respect to the pulse wave propagation velocities, as calculated from the pulse wave propagation velocities at each frequency calculated in step S142 (step S144). In parallel with or following the process of step S144, the CPU 10 calculates the degree of the frequency interval of the fluctuation appearing in the pulse wave propagation velocities for the frequency characteristics with respect to the pulse wave propagation velocities, as calculated from the pulse wave propagation velocities at each frequency calculated in step S142 (step S146). Note that it is also possible to carry out only one of steps S144 and S146.

Next, the CPU 10 determines whether or not conditions that indicate an arterial aneurysm may be present are met based on the information calculated in step S144 and/or step S146 (step S148).

More specifically, the CPU 10 determines whether or not the degree of variation in the pulse wave propagation velocities calculated in step S144 exceeds a predetermined threshold, or whether or not the frequency interval of the fluctuation appearing in the pulse wave propagation velocities calculated in step S146 is less than a predetermined threshold frequency.

In the case where the conditions that indicate an arterial aneurysm may be present are met (YES in step S148), the CPU 10 determines that a predetermined pathologic change such as an arterial aneurysm may be present in the vascular pathway from the heart of the measurement subject 200 to the measurement locations where the pressure cuffs 24a and 24b are attached, and outputs that evaluation result to the display unit 4 (step S150). Furthermore, the CPU 10 outputs information indicating the size of the arterial aneurysm estimated to be present to the display unit 4 based on the value of the frequency interval of the fluctuation appearing in the pulse wave propagation velocities calculated in step S146 (step S152). After this, the measurement process ends.

On the other hand, in the case where the conditions that indicate an arterial aneurysm may be present are not met (NO in step S148), the CPU 10 determines that a predetermined pathologic change such as an arterial aneurysm is unlikely to be present in the vascular pathway from the heart of the measurement subject 200 to the measurement locations where the pressure cuffs 24a and 24b are attached, and outputs that evaluation result to the display unit 4 (step S154). After this, the measurement process ends.

g4. Advantages

According to the present embodiment, the presence/absence of a pathologic change such as an arterial aneurysm can be determined simply by measuring pulse wave signals from the lower extremities and the upper extremities of a measurement subject.

Accordingly, arterial aneurysm diagnoses can be made using a simpler configuration and a simpler procedure. Furthermore, the present embodiment employs the pulse wave propagation velocity (PWV), which has been used in diagnoses thus far, and thus it is easy to integrate this method with existing diagnosis methods.

H. Other Embodiments

A measurement method for evaluating an arterial aneurysm that can occur in a vascular pathway according to the aforementioned embodiments may be implemented by executing a program. Such a program can be stored in a computer-readable recording medium such as a flexible disk, a CD-ROM (compact disk read-only memory), a ROM, a RAM, a memory card, or the like that is read by a computer, and can be provided as a program product. Alternatively, the program can be stored in a recording medium such as a hard disk mounted within a computer, and can be provided in such form as a program. Further still, the program can also be downloaded via a network, and can be provided in such form as a program.

Note that the program according to the present embodiment may be called and executed at a predetermined timing as a predetermined arrangement of required program modules among modules provided as part of a computer operating system (OS). In this case, the stated modules are not included in the program itself, and the processing is executed in cooperation with the OS. Programs that do not include such modules can also fall within the scope of the program according to the present embodiment.

In addition, the program according to the present embodiment may be provided having been incorporated into a part of another program. In such a case as well, modules included in the stated other program are not included within the program itself, and the processing is executed in cooperation with the other program. Such a program that is incorporated into another program can also fall within the scope of the program according to the present embodiment.

The program product that is provided is installed in a program storage unit such as a hard disk and executed. Note that the program product includes the program itself and the recording medium in which the program is stored.

Note that the embodiments disclosed above are to be understood as being in all ways exemplary and in no way limiting. The scope of the present invention is defined not by the aforementioned descriptions but by the scope of the appended claims, and all changes that fall within the same essential spirit as the scope of the claims are intended to be included therein as well.

INDUSTRIAL APPLICABILITY

The aforementioned embodiments make it possible to screen for and estimate the size of an arterial aneurysm through a comparatively simple configuration and procedure, and can be used to detect aortic aneurysms in the abdominal area, the chest area, and so on; the present invention can be applied in existing medical devices and the like.

REFERENCE SIGNS LIST 2 processing unit
4 display unit
6 operating unit
10 CPU
12 ROM
14 RAM
20a, 20b measurement unit
22a, 22b, 27a, 27b tube
24a, 24b pressure cuff
25a, 25b pressure pump
26a, 26b pressure adjustment valve
28a, 28b pressure sensor
30a, 30b, 32a, 32b frequency transform unit
31a, 31b frequency selection unit
40, 41, 42, 43 comparison unit
40a phase difference characteristic calculation unit
41a phase delay time calculation unit
42a gain characteristic calculation unit
43a calculation unit
50 determination unit
50a statistical processing unit
51a phase angle setting unit
60 output unit
100 measurement device

The invention claimed is:

1. A measurement device comprising:
a first pressure cuff comprising a first cuff pressure sensor configured to detect transmitted pressure, as a first pulse wave signal, at a first measurement location in a first vascular pathway connecting the heart of a measurement subject to an area where an abdominal arterial aneurysm is predicted to occur;
a second pressure cuff comprising a second cuff pressure sensor configured to detect transmitted pressure, as a second pulse wave signal, at a second measurement location in a second vascular pathway connecting the heart of the measurement subject to an area that is different from the area where the abdominal arterial aneurysm is predicted to occur;
a display; and
at least one processor configured to:
receive, from the first pressure cuff, the first pulse wave signal on the basis of a first pressure sensor detection result;
receive, from the second pressure cuff, the second pulse wave signal on the basis of a second pressure sensor detection result, the first pulse wave signal and the second pulse wave signal being detected by measuring voltage changes that arise due to changes in an impedance when a constant current is applied to the first measurement location where the first pressure cuff is located and the second measurement location where the second pressure cuff is located, respectively;
transform the received first pulse wave signal and the received second pulse wave signal into first phase characteristics, and second phase characteristics, respectively, which include frequency-domain information covering different frequencies;
compare the first phase characteristics with the second phase characteristics;
produce phase difference characteristics therebetween in each frequency of the different frequencies;
calculate a regression line based on the phase difference characteristics;
determine a degree of variation of the phase difference characteristics for each frequency from the regression line;
compare the degree of variation with a predetermined threshold; and
control the display to display:
when the degree of variation is greater than the predetermined threshold, an indication of a possibility of presence of abdominal arterial aneurysm; and
when the degree of variation is less than the predetermined threshold, an indication that presence of abdominal arterial aneurysm is low.

2. The measurement device according to claim 1, wherein the at least one processor is further configured to: determine the degree of variation based on an area between the regression line and the phase difference characteristics.

3. The measurement device according to claim 1, wherein the at least one processor is further configured to: determine the degree of variation based on a shift amount of the phase difference characteristics from the regression line.

4. A measurement method comprising:
receiving, by at least one processor from a first pressure cuff comprising a first pressure sensor configured to detect transmitted pressure, as a first pulse wave signal, at a first measurement location in a first vascular pathway connecting the heart of a measurement subject to an area where an abdominal arterial aneurysm is predicted to occur;
receiving, by the at least one processor from a second pressure cuff comprising a second pressure sensor configured to detect transmitted pressure, as a second pulse wave signal, at a second measurement location in a second vascular pathway connecting the heart of the measurement subject to an area that is different from the area where the abdominal arterial aneurysm is predicted to occur, the first pulse wave signal and the second pulse wave signal being detected by measuring voltage changes that arise due to changes in an impedance when a constant current is applied to the first measurement location where the first pressure cuff is located and the second measurement location where the second pressure cuff is located, respectively;
transforming, by the at least one processor, the received first pulse wave signal and the received second pulse wave signal into first phase characteristics, and second phase characteristics, respectively, which include frequency-domain information covering different frequencies;
comparing, by the at least one processor, the first phase characteristics with the second phase characteristics;
producing, by the at least one processor, phase difference characteristics therebetween in each frequency of the different frequencies;
calculating, by the at least one processor, a regression line based on the phase difference characteristics;
determining, by the at least one processor, a degree of variation of the phase difference characteristics for each frequency from the regression line;
comparing, by the at least one processor, the degree of variation with a predetermined threshold; and
control a display to display:
when the degree of variation is greater than the predetermined threshold, a first indication of a possibility of presence of an abdominal arterial aneurysm in the first vascular pathway; and
when the degree of variation is less than the predetermined threshold, a second indication, which is different from the first indication and that indicates that a possibility of presence of abdominal arterial aneurysm in the first vascular pathway is low.

5. A non-transitory computer readable recording medium storing computer program code that, when executed by a computer causes the computer to:
receive, from a first pressure cuff comprising a first pressure sensor configured to detect transmitted pressure, as a first pulse wave signal, at a first measurement location in a first vascular pathway connecting the heart of a measurement subject to an area where an abdominal arterial aneurysm is predicted to occur;
receive, from a second pressure cuff comprising a second pressure sensor configured to detect transmitted pressure, as a second pulse wave signal, at a second measurement location in a second vascular pathway connecting the heart of the measurement subject to an area that is different from the area where the abdominal arterial aneurysm is predicted to occur, the first pulse wave signal and the second pulse wave signal being detected by measuring voltage changes that arise due to changes in an impedance when a constant current is applied to the first measurement location where the first pressure cuff is located and the second measurement location where the second pressure cuff is located, respectively;
transform the received first pulse wave signal and the received second pulse wave signal into first phase characteristics, and second phase characteristics, respectively, which include frequency-domain information covering different frequencies;
compare the first phase characteristics with the second phase characteristics;
produce phase difference characteristics therebetween in each frequency of the different frequencies;
calculate a regression line based on the phase difference characteristics;
determine a degree of variation of the phase difference characteristics for each frequency from the regression line;
compare the degree of variation with a predetermined threshold; and
control a display to display:
when the degree of variation is greater than the predetermined threshold, a first indication of a possibility of presence of an abdominal arterial aneurysm in the first vascular pathway; and
when the degree of variation is less than the predetermined threshold, a second indication, which is different from the first indication and that indicates that a possibility of presence of abdominal arterial aneurysm in the first vascular pathway is low.

6. The measurement device according to claim 1, wherein the at least one processor is further configured to: determine the degree of variation based on a frequency interval between adjacent extreme values of the phase difference characteristics.

7. The measurement device according to claim 1, wherein the first pressure cuff is configured to be attached to one of the lower extremities and the second pressure cuff is configured to be attached to one of the upper extremities.

8. The measurement device according to claim 1, wherein the first pressure cuff is configured to be attached to an ankle area that includes the periphery of the anterior tibial artery of the measurement subject.

9. The measurement device according to claim 1, wherein the second pressure cuff is configured to be attached to an upper arm area including the periphery of the brachial artery of the measurement subject.

10. The measurement device according to claim 1, wherein the first and second pressure cuffs are inflated, thereby pressurizing the corresponding measurement areas, to allow for the pressure changes resulting from pulse waves at the measurement areas to be transmitted.

11. The measurement device according to claim 1, wherein the at least one processor is further configured to: determine the presence/absence and/or size of an arterial aneurysm based on a number of times the phase difference characteristics intersect with a phase angle calculated based on the average of phase delay times at each frequency.

12. The measurement device according to claim 1, wherein the at least one processor is further configured to: determine the presence/absence and/or size of an arterial aneurysm based on the frequency interval where the phase difference characteristics intersect with a phase angle calculated based on the average of the phase delay times at each frequency.

* * * * *